(12) United States Patent
McDaniel et al.

(10) Patent No.: US 8,916,015 B2
(45) Date of Patent: Dec. 23, 2014

(54) TAMPON METHOD OF MANUFACTURE

(75) Inventors: Mary Lou McDaniel, Appleton, WI (US); John David Amundson, Greenville, WI (US); Steven Craig Gehling, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 403 days.

(21) Appl. No.: 13/333,311

(22) Filed: Dec. 21, 2011

(65) Prior Publication Data
US 2013/0160259 A1 Jun. 27, 2013

(51) Int. Cl.
*A61F 13/22* (2006.01)
*A61F 13/20* (2006.01)

(52) U.S. Cl.
CPC ........ *A61F 13/222* (2013.01); *A61F 13/2068* (2013.01); *A61F 13/2094* (2013.01); *A61F 13/2065* (2013.01); *A61F 13/2034* (2013.01); *A61F 13/2088* (2013.01)
USPC ...................... 156/252; 156/269; 604/385.17

(58) Field of Classification Search
None
See application file for complete search history.

(56) References Cited

U.S. PATENT DOCUMENTS

| | | |
|---|---|---|
| 2,073,410 A | 3/1937 | Thomas |
| 2,905,175 A | 9/1959 | Schwartz |
| 3,085,574 A | 4/1963 | Penksa |
| 3,610,243 A | 10/1971 | Jones, Sr. |
| 3,624,746 A | 11/1971 | Grad et al. |
| 3,794,029 A | 2/1974 | Dulle |
| 4,185,631 A | 1/1980 | McConnell |
| 4,212,301 A | 7/1980 | Johnson |
| 4,288,884 A | 9/1981 | Bahls |
| 4,335,720 A | 6/1982 | Glassman |
| 4,816,100 A * | 3/1989 | Friese ........................... 156/191 |
| 4,911,777 A * | 3/1990 | Truc et al. ..................... 156/252 |
| 5,004,467 A | 4/1991 | Hinzmann et al. |
| 5,047,024 A | 9/1991 | Glassman et al. |
| 5,112,348 A | 5/1992 | Glassman |
| 5,514,158 A | 5/1996 | Kanesaka |
| 5,584,827 A | 12/1996 | Korteweg et al. |
| 6,039,716 A | 3/2000 | Jessup et al. |
| 6,177,608 B1 | 1/2001 | Weinstrauch |
| 6,186,994 B1 | 2/2001 | Bowles et al. |
| 6,267,832 B1 * | 7/2001 | Choi .............................. 156/70 |
| 6,419,777 B1 | 7/2002 | Achter et al. |
| 6,458,072 B1 | 10/2002 | Zunker |
| 6,511,451 B1 * | 1/2003 | Schoelling et al. ............. 604/14 |
| 6,558,370 B2 | 5/2003 | Moser |

(Continued)

FOREIGN PATENT DOCUMENTS

| | | |
|---|---|---|
| EP | 0 685 213 A2 | 12/1995 |
| WO | WO 95/16423 A2 | 6/1995 |
| WO | WO 2006/016933 | 2/2006 |
| WO | WO 2010117309 A1 * | 10/2010 |

OTHER PUBLICATIONS

Co-pending U.S. Appl. No. 13/333,150, filed Dec. 21, 2011, by Mary Lou McDaniel for "Tampon. ".

*Primary Examiner* — Barbara J Musser
(74) *Attorney, Agent, or Firm* — Kimberly-Clark Worldwide, Inc.

(57) ABSTRACT

A pledget for a tampon having improved leakage prevention of bodily fluid after the tampon is inserted in the vagina. A method of manufacturing the pledget can include a step of bringing a contact member into communication with a fibrous material. The method can include a step of compressing the fibrous material into a pledget for a tampon.

8 Claims, 20 Drawing Sheets

(56) References Cited

U.S. PATENT DOCUMENTS

| | | |
|---|---|---|
| 6,719,743 B1 | 4/2004 | Wada |
| 6,743,212 B1 | 6/2004 | Pierson et al. |
| 6,840,927 B2 | 1/2005 | Hasse et al. |
| 7,192,421 B2 | 3/2007 | Hasse et al. |
| 7,338,462 B2 | 3/2008 | Minoguchi et al. |
| 7,845,380 B2 | 12/2010 | Binner et al. |
| 2003/0229328 A1 | 12/2003 | Costa |
| 2005/0256482 A1 | 11/2005 | Minoguchi et al. |
| 2005/0256484 A1 | 11/2005 | Chase et al. |
| 2006/0247592 A1 | 11/2006 | Schmidt-Forst et al. |
| 2007/0073257 A1 | 3/2007 | Buck et al. |
| 2007/0260211 A1 | 11/2007 | Schmidt-Forst et al. |
| 2008/0154174 A1 | 6/2008 | Costa |
| 2008/0154222 A1 | 6/2008 | Chaffringeon |
| 2008/0221502 A1 | 9/2008 | Binner et al. |
| 2008/0262463 A1 | 10/2008 | Noel et al. |
| 2009/0036859 A1 | 2/2009 | Dougherty, Jr. et al. |
| 2009/0281474 A1 | 11/2009 | Dougherty, Jr. et al. |
| 2011/0077612 A1 | 3/2011 | Jorgensen et al. |
| 2012/0053544 A1 | 3/2012 | Drevik |

\* cited by examiner 6 pt

TAMPON METHOD OF MANUFACTURE

BACKGROUND

Currently, there are two basic types of tampons used for feminine hygiene. The first type is a digitally insertable tampon which is designed to be inserted directly by the user's fingers. The second type is an applicator style tampon which is designed to be inserted with the aid of an applicator. Both types are usually made by folding or rolling one or more loosely associated rectangular strips of absorbent material into a blank and then compressing the blank into a cylindrically-shaped pledget. The pledget may or may not have a cover. In both types, a withdrawal string can be attached to the pledget. The combination of a pledget and a withdrawal string is considered a useable tampon product. The tampon can then be wrapped and packaged for sale. In the applicator style tampon, the tampons can be assembled into an applicator prior to being wrapped and packaged.

Tampons work by acquiring the vaginal fluids including menses where the outside surface of the tampon and vaginal wall contact. To ensure this contact, current tampons alter the vagina immediately upon insertion. This alteration contributes to early premature, "by-pass" leakage. After the tampon absorbs the vaginal fluids including menses, most tampons begin to expand uniformly and globally, further contributing to this leakage. At the same time, the tampon begins to become more flexible and conformable to allow better global/macro fit to the vagina. This predetermined and uniform tampon response that drives this global/macro expansion is governed by the tampon construction and materials.

Even when fluid is acquired locally and the deformational forces on the tampon by the vaginal environment are applied locally with current tampons, the construction or materials of the tampons inhibits or constrains their capacity to expand or adapt to give this local/micro fit. These constructions and materials force the entire tampon to respond to these local fluid acquisition and deformational forces through material connectivity or material stiffness.

When attempts are made to allow for more local adaptation in tampon constructions, their constructions do not acquire the fluids well because of inadequate contact area because they can't match the local contours of the vaginal wall or are not conformable enough to adapt to the women's individual local contours (e.g. folds and convolutions) found on the vaginal wall. In addition, these attempts create integrity issues with the tampons that lead to portions of the tampon remaining within the vagina after tampon removal. This inadequate contact is especially true during the wiping action of the vagina by the tampon when the tampon is inserted and removed.

Current tampon construction processes construct these inadequate tampons that have this predetermined and uniform tampon response. They create these constraints, inadequate contact area, and integrity issues in order to drive this predetermined and uniform tampon response and, therefore, limit the tampon from effectively responding locally. New construction processes will be needed to construct tampons that overcome the inadequacy of current tampons.

There remains a need for a tampon that responds locally to meet the individual protection needs of women and processes to make such tampons. There remains a need for a tampon that prevents leakage of body fluid after being inserted into a woman's vagina. There remains a need for a tampon that provides efficient utilization of the entire tampon structure during use. There remains a need for a tampon that provides a customized fit to the anatomy of a woman's vaginal cavity. There remains a need for a tampon that can deform and come into contact with the folds and convolutions of the walls of the vaginal cavity and acquire any contacted fluid.

SUMMARY

In an embodiment a method of manufacturing a pledget has the steps of providing a fibrous material, providing a contact member, incorporating at least two slits in the contact member to form a contact element in the contact member, bonding the contact member to the fibrous material, and compressing the combination of the fibrous material and the contact member. In an embodiment, the method further has the step of separating at least one individual unit from the fibrous material. In an embodiment, the method further has the step of rolling, stacking or folding the fibrous material. In an embodiment, the fibrous material is one of a nonwoven ribbon, a fleece, and a blank. In an embodiment, the method further has the step of providing a cover. In an embodiment, the method further has the step of bonding the contact member to the cover. In an embodiment, the contact member has a first edge and a second edge and the step of bonding the contact member to the fibrous material further has the step of bonding one of the first edge or the second edge to the fibrous material creating a bonded edge and a free edge. In an embodiment, the method further has the step of enclosing the contact member in an outer sheath. In an embodiment, the method further has the step of incorporating at least two slits in the outer sheath.

In an embodiment, a method of manufacturing a tampon has the steps of providing a fibrous material, providing a cover, providing a contact member, incorporating at least two slits in the contact member to form a contact element in the contact member, bonding the contact member to the cover, bonding the combination of the cover and the contact member to the fibrous material, and compressing the combination of the fibrous material, the cover and the contact member. In an embodiment, the method further has the step of separating at least one individual unit from the fibrous material. In an embodiment, the method further has the step of rolling, stacking or folding the fibrous material. In an embodiment, the fibrous material is one of a nonwoven ribbon, a fleece, and a blank. In an embodiment, the contact member has a first edge and a second edge and the step of bonding the contact member to the cover further has the step of bonding one of the first edge or the second edge to the cover to create a bonded edge and a free edge. In an embodiment, the method further has the step of enclosing the contact member in an outer sheath. In an embodiment, the method further has the step of incorporating at least two slits in the outer sheath.

In an embodiment, a method of manufacturing a cover has the steps of providing a cover ribbon, providing a contact member comprising a first edge and a second edge, bonding one of the first edge or the second edge of the contact member to the cover ribbon to create a combined unit of cover ribbon and contact member, and separating the combined unit of cover ribbon and contact member from a remainder of the cover ribbon. In an embodiment, the method further has the step of enclosing the contact member in an outer sheath. In an embodiment, the method further has the step of incorporating at least two slits into the contact member to form a contact element.

DETAILED DESCRIPTION

The tampon of the current disclosure is designed to be inserted above the introital region of a woman's vagina and is designed to function so as to intercept the fluid flow of menses, blood, and other body fluids and prevent the fluid from exiting the vagina. While the pledgets and tampons of the current disclosure are described for use as a menstrual device, it will be readily apparent that the pledgets and tampons can also be used as any other suitable vaginal insert, such as a pessary. Likewise, while the pledgets and tampons of the current disclosure are generally described as being "absorbent," it will be readily apparent that the pledgets and tampons may be coated or otherwise treated to be partially or completely non-absorbent. The pledget and tampon of the current disclosure can have a contact member which can have a contact element. In an embodiment, the contact element can be small and can be created by slitting flexible materials which can allow the pledget and the tampon to respond locally to the changes in the vaginal environment and can effectively acquire fluid locally to accommodate the uniqueness of a woman's vaginal environment and her period.

Figure 1:
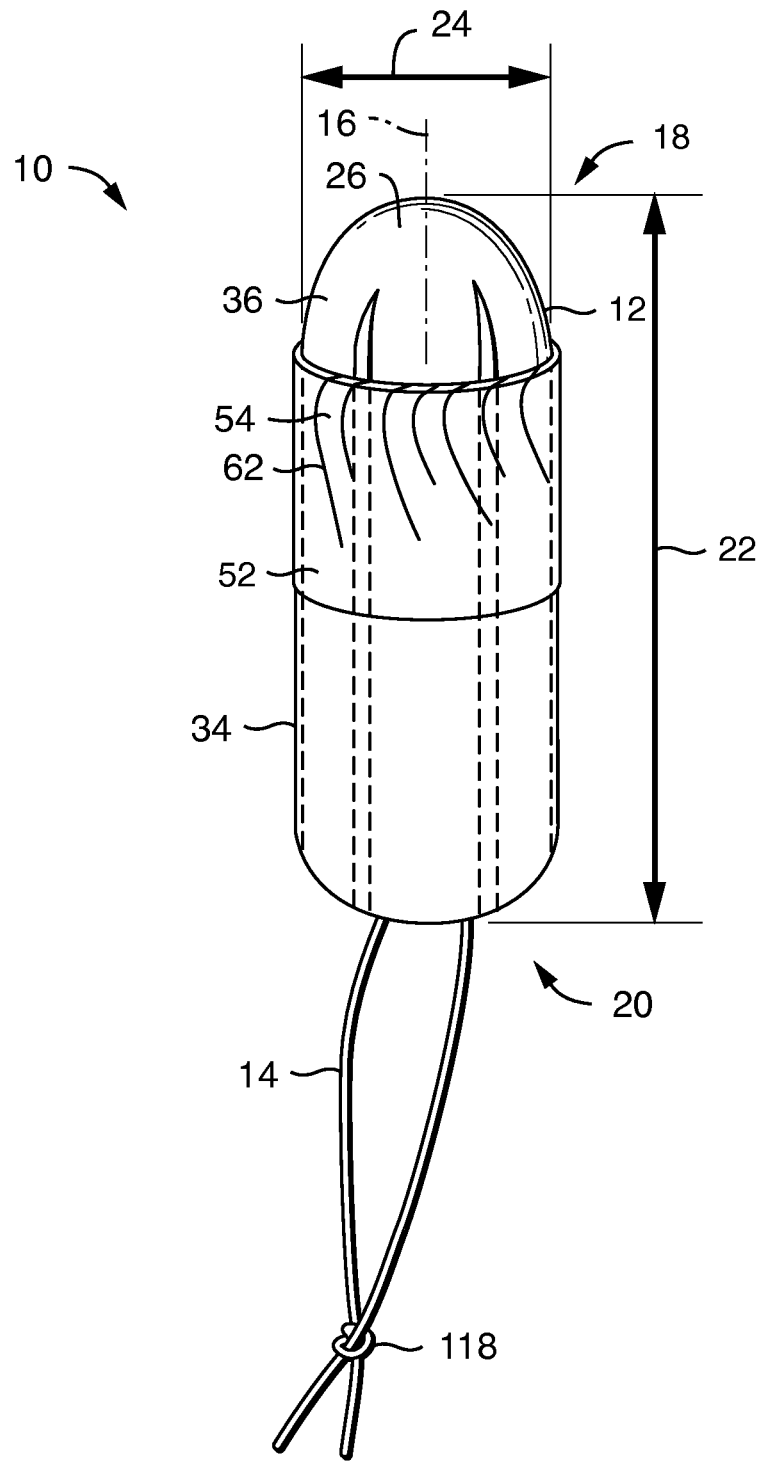
FIG. 1 is a perspective view of an embodiment of a tampon.

An embodiment of a tampon 10 of the current disclosure is illustrated in FIG. 1. The tampon 10 is designed to be inserted into a woman's vaginal cavity to prevent menses from exiting the vaginal opening by contacting and absorbing the flow of menses. The term "menses," as used herein, includes blood, tissue debris, and other bodily fluids emitted from the vaginal opening. The tampon 10 can have a compressed, generally cylindrical shaped pledget 12 and a withdrawal aid 14. In some embodiments, the generally cylindrical shape of the pledget 12 can have a cross-section that is at least one of an oval, circle, square, rectangle, or any other cross-sectional shape known in the art. The term "cross-section" refers herein to the plane which extends laterally through the tampon 10, and which is orthogonal to the longitudinal axis 16 of the pledget 12, and consequently, of the tampon 10. The tampon 10 can have an insertion end 18 and a withdrawal end 20. The tampon 10 can have a length 22 wherein the length 22 is the measurement of the tampon 10 along the longitudinal axis 16 originating at one end (insertion or withdrawal) of the tampon 10 and ending at the opposite end (insertion or withdrawal) of the tampon 10. In some embodiments, the tampon 10 can have a length 22 from about 30 to about 60 mm. The tampon 10 can have a width 24, which unless otherwise stated herein, can correspond to the greatest cross-sectional dimension along the longitudinal axis 16 of the tampon 10. In some embodiments, the tampon 10 can have a compressed width 24 prior to usage from about 2, 5, or 8 to about 20 or 30 mm. The tampon 10 may be straight or non-linear in shape, such as curved along the longitudinal axis 16.

As noted above, the tampon 10 can have a pledget 12. The pledget 12 can have an absorbent core 26 which can be formed from a blank 28, such as a softwind, wherein the blank 28 can be formed from a fleece 30. The fleece 30 can be formed from a nonwoven ribbon 32 composed of fibrous materials 138. It is to be understood, that each of the nonwoven ribbon 32, the fleece 30, the blank 28, the absorbent core 26, the pledget 12 can be formed from fibrous material 138. The fleece 30 can be any size and thickness that can ultimately be compressed into a pledget 12 having a vaginally insertable shape. In an embodiment, the fleece 30 can be a laminar structure that can have individual distinct layers of absorbent material. In an embodiment in which the fleece 30 has a laminar structure, the layers can be formed from a single absorbent material and/or from different absorbent materials. In an embodiment, the size of the fleece 30 can range from about 40 mm to about 100, 200, 250 or 300 mm in length and from about 40 mm to about 80 mm in width. In an embodiment, the overall basis weight of the fleece 30 can range from about 15, 20, 25, 50, 75, 90, 100, 110, 120, 135 or 150 gsm to about 1,000, 1,100, 1,200, 1,300, 1,400, or 1,500 gsm.

The fleece 30, and consequently, the pledget 12 of the tampon 10, may be constructed from a nonwoven ribbon 32 of absorbent materials such as fibrous materials 138. Such absorbent materials can include, but are not limited to, natural and synthetic fibers such as, but not limited to, polyester, acetate, nylon, cellulosic fibers such as wood pulp, cotton, rayon, viscose, LYOCELL® such as from Lenzing Company of Austria, or mixtures of these or other cellulosic fibers. Natural fibers can include, but are not limited to, wool, cotton, flax, hemp and wood pulp. Wood pulps can include, but are not limited to, standard softwood fluffing grade such as CR-1654 (US Alliance Pulp Mills, Coosa, Ala.). Pulp may be modified in order to enhance the inherent characteristics of the fibers and their processability. Crimping can be imparted to the fibers by any means deemed suitable by one of ordinary skill Curl may be imparted to the fibers by suitable methods such as, for example, chemical treatment or mechanical twisting. Curl can be imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Pulp may also be stiffened by the use of heat or caustic treatments such as mercerization. Examples of these types of fibers include NHB416, which is a chemically cross-linked southern softwood pulp fiber which enhances wet modulus, available from Weyerhaeuser Corporation of Tacoma, Wash. Other non-limiting examples of useful pulps are debonded pulp (NF405) and non-debonded pulp (NB416) also from Weyerhaeuser. HPZ3 from Buckeye Technologies, Inc. of Memphis, Tenn., is an example of a fiber that has a chemical treatment that sets in a curl and twist, in addition to imparting added dry and wet stiffness and resilience to the fiber. Another suitable pulp is Buckeye HP2 pulp and still another is IP Supersoft from International Paper Corporation. The absorbent materials can include any suitable blend of fibers. For example, the absorbent fibers can be formed from cellulose fibers such as cotton and rayon. The absorbent fibers can be 100 wt % cotton, 100 wt % rayon, or a blend of cotton and rayon. In some embodiments, the cellulose fibers may be modified for super-absorbency.

In an embodiment, the fibers can have a staple length of from about 5, 10, 15 or 20 mm to about 30, 40 or 50 mm. In an embodiment, the fibers can have a fiber size of from about 15 microns to about 28 microns. In an embodiment, the fibers can have a denier of from about 1 or 2 to about 6. Denier is a unit of fineness of yarn based on a standard of 50 milligrams (mg) for 450 meters of yarn. The fibers can have a circular, bi-lobal or tri-lobal cross-sectional configuration or any other configuration known to those skilled in the art. A bi-lobal configuration can have a cross-sectional profile which can look like a dog bone while a tri-lobal configuration can have a cross-sectional profile which can look like a "Y." In an embodiment, the fibers can be bleached. In an embodiment, the fibers can have a color.

In an embodiment, the nonwoven ribbon 32 can contain fibers such as binder fibers. In an embodiment, the binder fibers can have a fiber component which will bond or fuse to other fibers in the nonwoven ribbon 32. Binder fibers can be natural fibers or synthetic fibers. Synthetic fibers include, but are not limited to, those made from polyolefins, polyamides, polyesters, rayon, acrylics, viscose, superabsorbents, LYOCELL® regenerated cellulose and any other suitable synthetic fiber known to those skilled in the art. Non-limiting examples of polyolefins include, but are not limited to, polyethylene such as Dow Chemical's ASPUN® 681 1A linear low density polyethylene, 2553 LLDPE and 25355 and 12350 high density polyethylene. The polyethylenes can have melt flow rates, respectively, of about 26, 40, 25, and 12. Non-limiting examples of fiber forming polypropylenes include, but are not limited to, Exxon Chemical Company's ESCORENE® PD 3445 polypropylene and Montell Chemical Company's PF304. Another example of a fiber can be a bi-component polyester sheath and polyethylene core known as T255 made by Trevira of Germany. Other non-limiting examples of meltable bicomponent fibers include, but are not limited to, fibers available from Unitika of Japan, such as, for example, Unitika MELTY 4080, and 6080 fibers, having either polyester sheaths or cores and polyethylene sheaths or cores. Another example includes, but is not limited to, fibers available from Fibervisions under the designation ETC Bounce fiber line, such as PET/PE fibers of about 2.2 decitex and about 40 mm staple fiber length. Non-limiting examples of rayon fibers include 1.5 denier Merge 18453 fibers from Accordis Cellulose Fibers Inc. of Axis, Ala. The fibers can be treated by conventional compositions and/or processes to enable or enhance wettability.

Various methods known to those skilled in the art can be used to prepare the nonwoven ribbon 32. Such methods can include, but are not limited to, airlaying, carding, wetlaying, needlepunching, mechanical entanglement, hydroentangling, and any other known method deemed suitable by one of ordinary skill. In an embodiment, a bonded carded web can be made from staple fibers. In such an embodiment, the fibers can be longer than about 20, 30 or 35 mm. The fibers can be purchased in bales which can be placed in a picker to separate the fibers. The fibers can then be sent through a combing or carding unit, which can further break apart and align the staple fibers in the machine direction to form a generally machine direction-oriented fibrous nonwoven web. Once the web is formed, it can then be bonded by one or more of several known bonding methods, such as through air bonding or pattern bonding. In an embodiment, a dry laid web can be made from staple fibers. In such an embodiment, the fibers can be about 20 mm or longer. In dry laying, fibers or tufts of fibers of a first type (e.g., absorbent fibers and/or binder fibers) can be fed to a first rotating vacuum drum and fibers or tufts of fibers of a second type (e.g., absorbent fibers and/or binder fibers) can be fed to a second rotating vacuum drum. The fibers can then be laid down by suction to form mats of fibers. The mats of fibers can be doffed from the vacuum drums and combed via rotating lickerins. The lickerins can have peripheral teeth which can comb the fibers from the mat. The combed fibers can be doffed from the lickerins via centrifugal force and placed into a fiber mixing and expansion chamber. The mixed fibers can be placed on a vacuum screen to form a random fiber web comprising the first and second fiber types. The flow and velocity of each independent fiber stream can be controlled to provide the desired quantity of each fiber type.

In an embodiment in which binder fibers are present, the binder fibers can be activated to create a three-dimensional fiber matrix. In such an embodiment, the activation can be completed by any suitable heating step including, but not limited to, convection heating, through air heating, super-heated steam, microwave heating, radiant heating, radio frequency heating, and the like, and combinations thereof. In some embodiments, the activation can be accomplished by heating the nonwoven ribbon 32 at a temperature of from about 240° F. to about 330° F. (about 115 to about 165° C.) to activate the binder fibers. It is to be understood that the bonding temperature selected should be selected based upon the materials which are being bonded together. Without being bound by theory, it is believed that during activation, the binder fibers can soften and become tacky and, therefore, bind to adjacent fibers creating a three-dimensional fiber matrix. It is believed that the three-dimensional fiber matrix can stabilize the nonwoven ribbon 32 and can create a liquid stable network. It is to be understood that an additional component or finish can be added to the fibers to facilitate bonding of absorbent materials which are not necessarily compatible.

In an embodiment, the activation can be followed by a cooling step which can utilize any suitable means for reducing the temperature of the nonwoven ribbon 32. In an embodiment, the nonwoven ribbon 32 can be cooled by allowing the nonwoven ribbon 32 to return to ambient temperature over a period of time. In an embodiment, the nonwoven ribbon 32 can be cooled by chill rolls, cooling chambers, blowing conditioned air, or the like, and combinations thereof. In an embodiment, the cooling step can occur prior to compression of the nonwoven ribbon 32 to establish a wet-stable three-dimensional structure.

In some embodiments, the nonwoven ribbon 32 can be further manipulated such as, for example, being folded, corrugated, or otherwise processed. The nonwoven ribbon 32 can be separated into individual units of fleece 30. The separation of the nonwoven ribbon 32 into individual units of fleece 30 can occur by any suitable method such as stretching, perforating, cutting such as with the use of a die cutter or a knife cutter, and the like. The individual units of fleece 30 can then be rolled, stacked, folded, or otherwise manipulated into blanks 28 before compressing the blanks 28 into pledgets 12.

In various embodiments, the fleece 30 and the resultant pledget 12 can have any suitable combination and ratio of fibers. In an embodiment, the fleece 30 and the resultant pledget 12 can include from about 70 to about 95 wt % absorbent fibers and from about 5 to about 30 wt % binder fibers. In an embodiment, the fleece 30 and the resultant pledget 12 can include from about 80 to about 90 wt % absorbent fibers and from about 10 to about 20 wt % binder fibers. In an embodiment, the fleece 30 and the resultant pledget 12 can include about 85 wt % absorbent fibers and about 15 wt % binder fibers. In an embodiment, the fleece 30 and the resultant pledget 12 can include from about 80 to about 90 wt % trilobal viscose rayon fibers and from about 10 to about 20 wt % bicomponent binder fibers. In an embodiment, the fleece 30 and the resultant pledget 12 can include 85 wt % trilobal viscose rayon fibers and about 15 wt % bicomponent binder fibers. In an embodiment, the fleece 30 and the resultant pledget 12 can include greater than about 70, 80, 90, 95, 97, or 99 wt % absorbent fibers.

With reference to FIGS. 2-6, in various embodiments, a cover 34 can be provided. As used herein, the term "cover" relates to materials that are in communication with and cover or enclose surfaces, such as, for example, a body facing surface 36, an interior surface 38, or combination thereof, of an absorbent core 26 of the resultant pledget 12 and reduce the ability of portions (e.g., fibers and the like) from becoming separated from the pledget 12 or the tampon 10 and being left behind upon removal of the tampon 10 from the woman's vagina. In various embodiments, the cover 34 can be a fluid-permeable cover 34. By "fluid-permeable" it is meant that body fluid is able to pass through the cover 34. The cover 34 can be hydrophobic or hydrophilic. By "hydrophilic" it is meant that the cover 34 has an affinity for absorbing or tending to combine with water. By "hydrophobic" it is meant that the cover 34 is antagonistic to or tending not to combine with water. The cover 34 can also be treated with a surfactant or other material to make it hydrophilic or to make it more hydrophilic.

Figure 2:
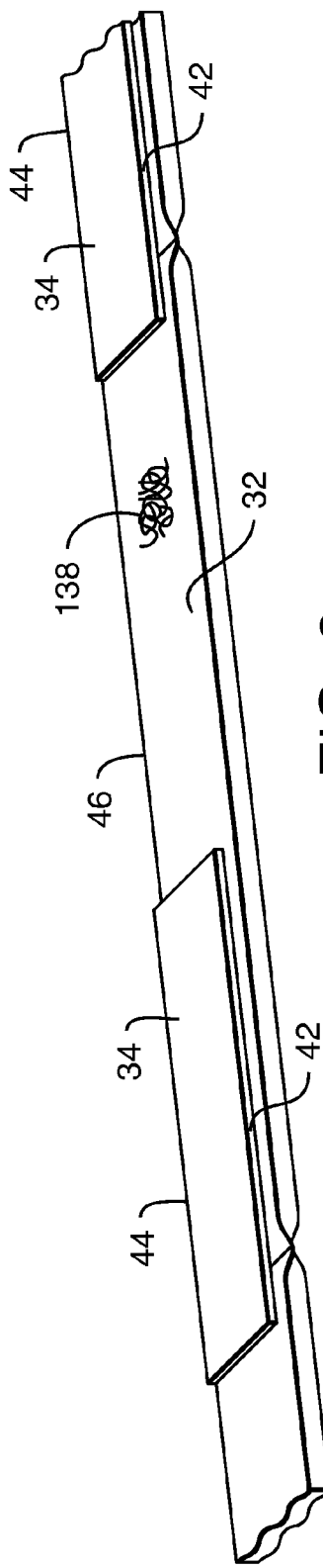
FIG. 2 is a perspective view of an embodiment in which a cover is bonded to a nonwoven ribbon.
Figure 3:
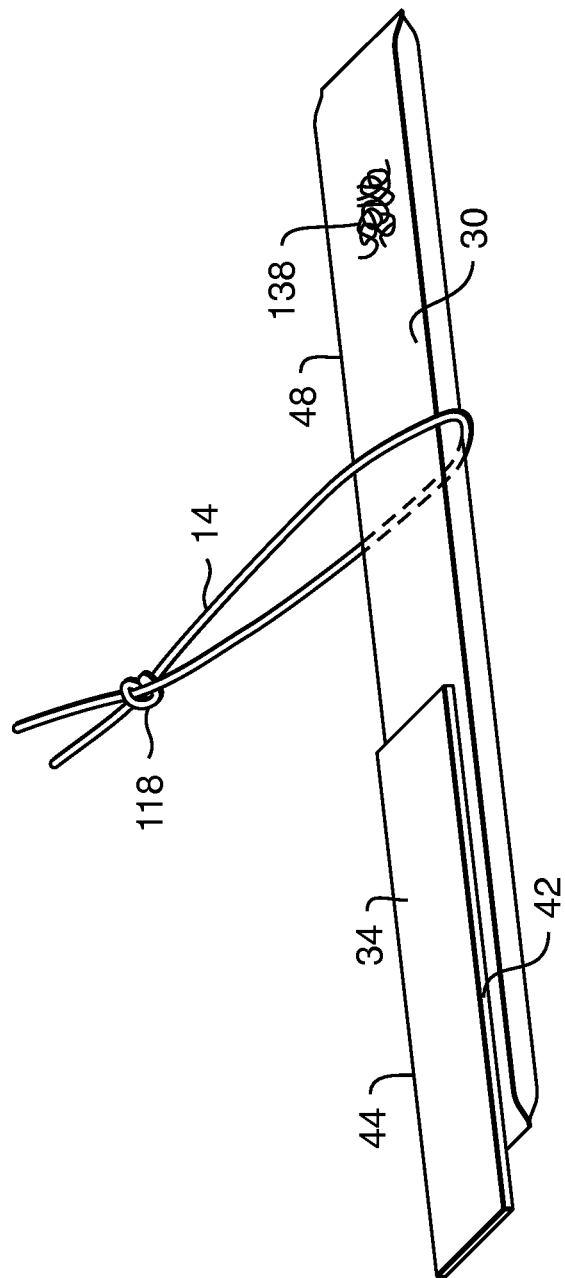
FIG. 3 is a perspective view of an embodiment in which a cover is bonded to a fleece.
Figure 4:
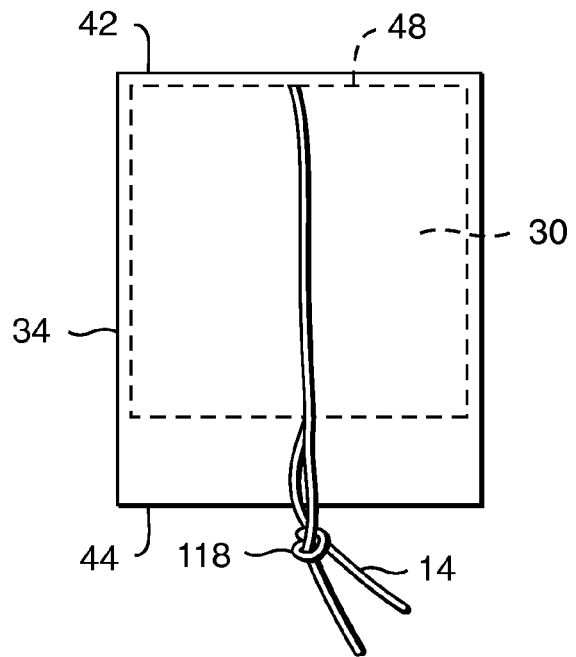
FIG. 4 is a top view of an embodiment in which a cover is bonded to a fleece.
Figure 5:
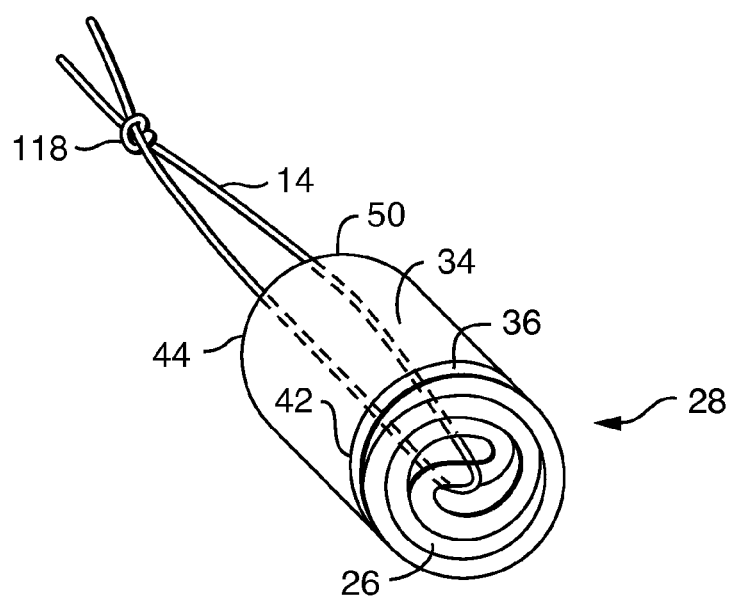
FIG. 5 is a perspective view of an embodiment in which a cover is bonded to a blank, such as a blank formed by radial winding of a fleece.
Figure 6A:
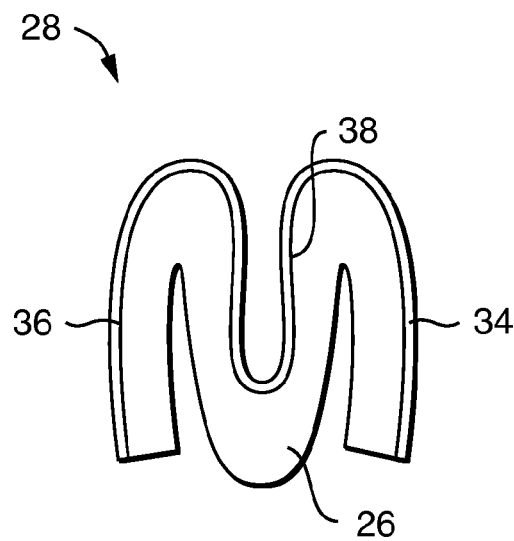
FIG. 6A is an end view of an embodiment in which a cover is bonded to a blank, such as a blank formed by compression of a fleece.
Figure 6B:
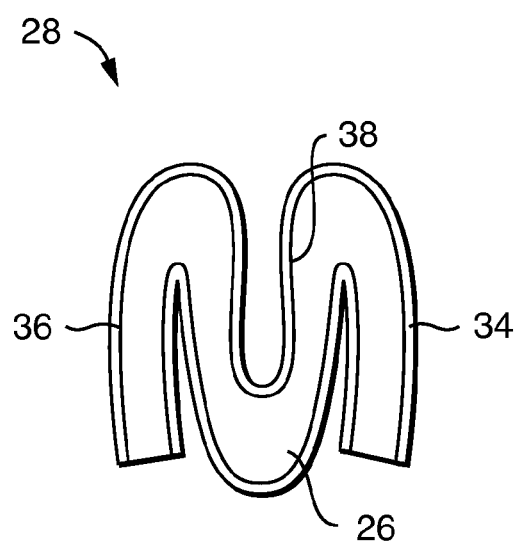
FIG. 6B is an end view of an embodiment in which two covers are bonded to a blank, such as a blank formed by compression of a fleece.

As will be described herein, the cover 34 can be bonded with: the nonwoven ribbon 32 prior to separation into individual units of fleece 30 (as illustrated in FIG. 2), an individual unit of fleece 30 (as illustrated in FIGS. 3 and 4), a blank 28 which has been formed from a fleece 30 (as illustrated in FIGS. 5, 6A and 6B), or to the pledget 12 following compression of the blank 28. In an embodiment in which the cover 34 is bonded with a pledget 12 following compression of a blank 28, the cover 34 can be extensible such that the tampon 10 can expand within the vaginal cavity.

The cover 34 can, therefore, be bonded to the nonwoven ribbon 32, a fleece 30, a blank 28, or the resultant pledget 12. The terms "bonded" or "bonding" refer herein to the joining, adhering, connecting, attaching or the like of two elements. Two elements will be considered bonded together when they are bonded directly to one another or indirectly to one another, such as when each is directly bonded to intermediate elements. The bonding can occur by any method deemed suitable including, but not limited to, adhesives, ultrasonic bonds, thermal bonds, pressure bonds, mechanical entanglement, hydroentanglement, microwave bonds, or any other conventional technique. The bonding can extend continuously along the length of bonding, or it may be applied in an intermittent fashion at discrete intervals.

In various embodiments, the cover 34 can be formed from nonwoven materials or apertured films. The nonwoven materials can include, but are not limited to, materials such as natural fibers, synthetic fibers, or blends of natural and synthetic fibers. Natural fibers include, but are not limited to, rayon, cotton, wood pulp, flax, and hemp. Synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. The cover 34 can be made by any number of suitable techniques such as, for example, being spunbond, carded, hydroentangled, thermally bonded, and resin bonded. In an embodiment, the cover 34 can be formed from an apertured thermoplastic film having either a two-dimensional or a three-dimensional thickness.

In an embodiment, the cover 34 can be a 12 gsm smooth calendared material made from bicomponent, polyester sheath and polyethylene core, fibers such as Sawabond 4189 available from Sandler AG, Schwarzenbach, Germany. In an embodiment, the cover 34 can be formed from a single piece of material. In an embodiment, the cover 34 can be formed from multiple discrete pieces of material which are bonded together. In an embodiment, the cover 34 can be bleached. In an embodiment, the cover 34 can have a color.

In an embodiment, the cover 34 can be treated with an aqueous solution to reduce frictional drag, to give the tampon 10 a permanent wettability, to enhance the ease of insertion into and withdrawal from a woman's vagina, and combinations thereof. In an embodiment, the cover 34 can be treated either before being rolled or folded up with the fleece 30 into a blank 28 or after the blank 28 has been formed and the cover 34 has been bonded with the blank 28.

Figure 7:
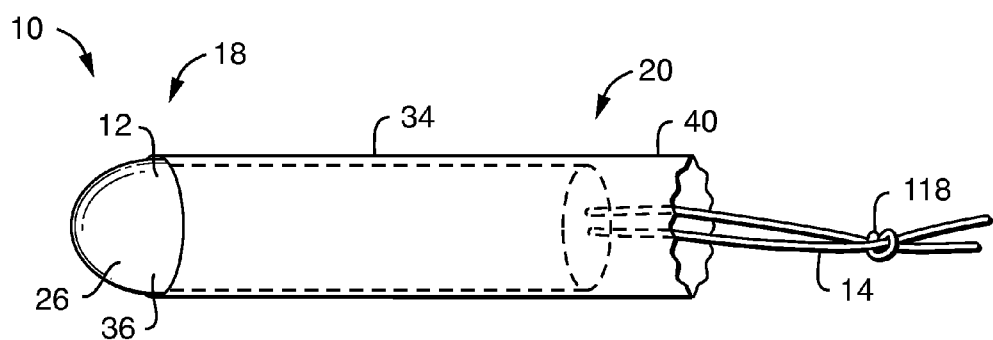
FIG. 7 is a side view of an embodiment of a tampon wherein the cover defines a skirt.

As illustrated in FIG. 5, in an embodiment, at least a portion of the cover 34 can cover a portion of the body facing surface 36 of a blank 28 and the resultant absorbent core 26 of a pledget 12. As illustrated in FIG. 6A, in an embodiment, at least a portion of the cover 34 can cover a portion of an interior surface 38 of a blank 28 and the resultant absorbent core 26 of the a pledget 12 when a fleece 30 is compressed, such as, for example, via side compression. As illustrated in FIG. 6A, in an embodiment, at least a portion of the cover 34 can cover a combination of the body facing surface 36 and the interior surface 38 of a blank 28 and the resultant absorbent core 26 of a pledget 12. The interior surface 38 of the blank 28 and of the resultant absorbent core 26 of a pledget 12 can result from folding, rolling, or otherwise manipulating the fleece 30 into the blank 28. It is to be understood that in an embodiment, the interior surface 38 of the absorbent core 26 of the pledget 12 may come into contact with the vaginal walls as the tampon 10 can expand when contacted by body fluids. The expansion of the tampon 10 can, therefore, cause exposure of the interior surface 38 of the pledget 12 to the vaginal walls and body fluid. As illustrated in FIG. 6B, in an embodiment two covers 34 can be in communication with a fleece 30 which can be compressed, such as, for example, via side compression, into a blank 28. As illustrated in FIG. 6B, in such an embodiment, at least a portion of each of the covers 34 can cover a portion of an interior surface 38 of a blank 28 and the resultant absorbent core 26 of a pledget 12. In such an embodiment, at least a portion of each of the covers 34 can cover a combination of the body facing surface 36 and the interior surface 38 of a blank 28 and the resultant absorbent core 26 of a pledget 12. In various embodiments, the cover 34 can extend beyond the withdrawal end 20 of the pledget 12 to form a skirt 40 as illustrated in FIG. 7. It is to be understood that, in an embodiment, the cover 34 can extend beyond the insertion end 18 of the pledget 12.

In an embodiment, the cover 34 can have two edges, 42 and 44. As noted above, the cover 34 can be bonded to a nonwoven ribbon 32, a fleece 30, a blank 28, or a pledget 12. In an embodiment, during the bonding process, at least one of the edges, 42 or 44, of the cover 34 can be substantially aligned with one edge of the nonwoven ribbon 32 (such as edge 46), one edge of the fleece 30 (such as edge 48), or one edge of the blank 28 (such as edge 50). In an embodiment, during the bonding process, the cover 34 can be bonded to the nonwoven ribbon 32, the fleece 30, the blank 28, or the pledget 12 so as to produce a spiral or helical pattern on the resulting pledget 12. As illustrated in non-limiting examples, such as in FIGS. 3-5, the two edges, 42 and 44, are illustrated in a direction that would be perpendicular to the longitudinal axis 16 of a resultant absorbent core 26 of a pledget 12. It is to be understood that the edges, 42 and 44, can also be positioned in a direction parallel to the longitudinal axis 16 of a resultant absorbent core 26 of a pledget 12 or at any other angle to the longitudinal axis 16 of an absorbent core 26 of a pledget 12 such as may occur if the cover 34 is spirally wound about the absorbent core 26 of a pledget 12. Thus, while the cover 34 and the edges, 42 and 44, may be discussed herein in an orientation perpendicular to the longitudinal axis 16 of an absorbent core 26 of a pledget 12, one of ordinary skill will be able to recognize how to provide a cover 34 and edges, 42 and 44, in an orientation parallel with the longitudinal axis 16 of an absorbent core 26 of a pledget 12 or in an orientation having any other angle in relation to the longitudinal axis 16 of an absorbent core 26 of a pledget 12.

In an embodiment, the cover 34 can have uniform properties. In an embodiment, the cover 34 can have non-uniform properties. In such an embodiment, the cover 34 can have regions with differing properties which can be coordinated to increase or decrease absorbency and/or level of expansion of the tampon 10. For example, a region can be more hydrophilic or hydrophobic in comparison to another region of the cover 34. In an embodiment, the hydrophilic region of the cover 34 could substantially cover the portion of the tampon 10 that would contact the menses first to increase menses absorption and as a result increase expansion of that portion of the tampon 10.

The regions of the cover 34 with differing properties may be produced by various methods. One example of a method is by treating the regions of the cover 34 with chemical finishes, such as hydrophilic or hydrophobic finishes that make the regions either more hydrophilic or more hydrophobic, respectively. The regions can also be mechanically altered. Any method known in the art of mechanically altering non-wovens or films can be used to provide a cover 34. Mechanically altering includes, but is not limited to, processes such as ring-rolling, corrugating, SELFing, and aperturing.

The composition of the cover 34 can also provide for differing properties of the cover 34. Different regions of the cover 34 can be produced from different materials. For example, one region of the cover 34 may have a higher concentration of rayon than another section of the cover 34 to make that region more hydrophilic. Materials could be selected for any property desired for a cover 34 known in the art, such as a selection of a material to provide a region of the cover 34 with greater extensibility. In an embodiment, the cover 34 may include multiple discrete pieces that are bonded together to form a single cover 34. The discrete pieces can have differing properties such as described above. In an embodiment, the discrete pieces of the cover 34 may form the different regions of the cover 34 such as described above. In such an embodiment, one discrete piece may form one region and another discrete piece may form a different region of the cover 34. The discrete pieces can be bonded by any method known to one of ordinary skill in the art, such as sewing, adhesive, thermal bonding, fusion bonding, or combinations thereof.

Figure 8:
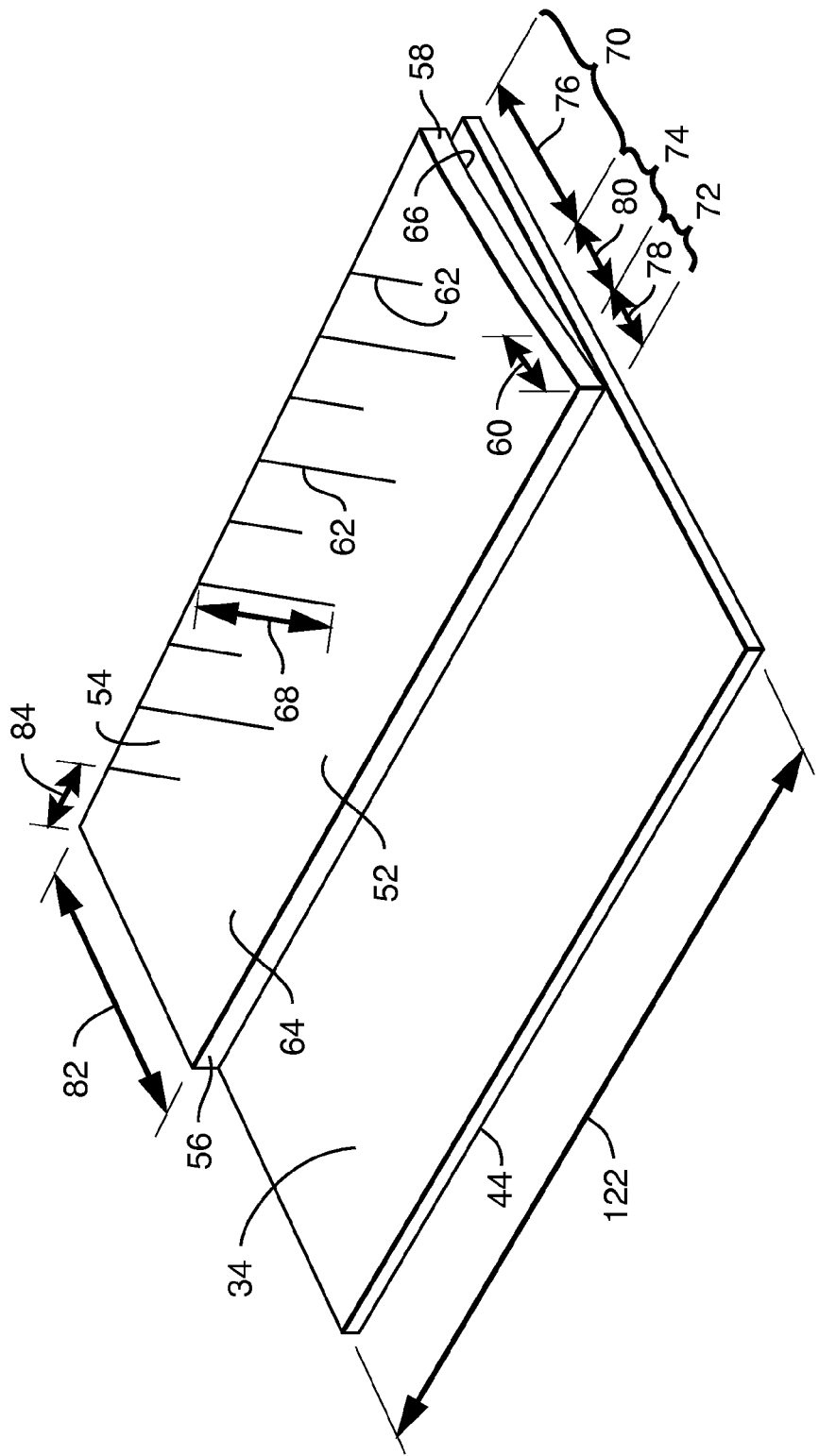
FIG. 8 is a perspective view of an embodiment of a contact member in communication with a cover.
Figure 17:
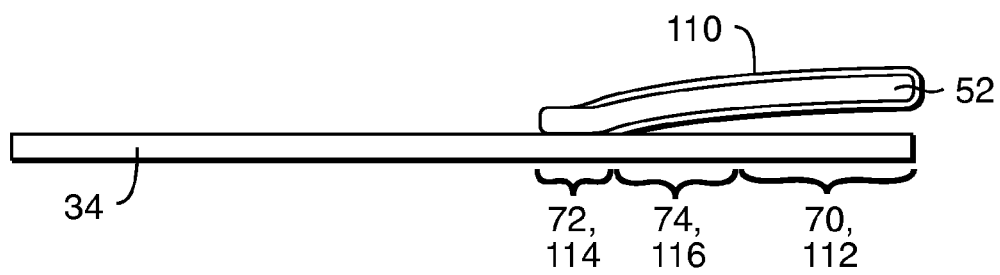
FIG. 17 is a side view of an embodiment of a contact member with an outer sheath and in communication with a cover.

FIG. 8 illustrates an embodiment in which a contact member 52 can be in communication with the cover 34. As will be described herein and as illustrated in FIG. 17, the contact member 52 can have an outer sheath 110. The contact member 52 can have at least one contact element 54. Without being bound by theory, it is believed that when the tampon 10 is in use the contact element 54 can at least partially expand outwardly from the tampon 10 when contacted by bodily fluids. It is believed that such expansion of the contact element 54 can reduce or prevent leakage of bodily fluids from the woman's vagina.

In various embodiments, the contact member 52 can be a fluid-permeable contact member 52. The contact member 52 can be hydrophobic or hydrophilic. The contact member 52 can also be treated with a surfactant or other material to make it hydrophilic or to make it more hydrophilic.

The contact member 52 can be formed from nonwoven materials or apertured films. The nonwoven materials can include, but are not limited to, materials such as natural fibers, synthetic fibers, or blends of natural and synthetic fibers. Natural fibers include, but are not limited to, rayon, cotton, wood pulp, flax, and hemp. Synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. Non-limiting examples of other acceptable materials include creped cellulose wadding, meltblown polymers including conform, chemically stiffened, modified or cross-linked cellulosic fibers, synthetic fibers such as crimped polyester fibers, peat moss, tissue including tissue wraps and tissue laminates, or any equivalent material or combinations of materials, or any mixtures of these. In an embodiment, the contact member 52 can be a laminar structure that can have individual distinct layers of absorbent material, non-absorbent material, moisture insensitive material, or combinations thereof. In such an embodiment, the individual distinct layers can be formed from a single material or from a combination of different materials. The contact member 52 can be made by any number of suitable techniques such as, for example, being spunbond, carded, hydroentangled, thermally bonded, and resin bonded. In an embodiment, the contact member 52 can be formed from an apertured thermoplastic film having either a two-dimensional or a three-dimensional thickness. In an embodiment, the contact member 52 can be bleached. In an embodiment, the contact member 52 can have a color.

In an embodiment, the contact member 52 can be bonded to the cover 34. The contact member 52 can be bonded to the cover 34 prior to or after the cover 34 is bonded to the nonwoven ribbon 32, the fleece 30, or the blank 28. The contact member 52 can be bonded to the cover 34 by any method suitable including, but not limited to, adhesives, ultrasonic bonds, thermal bonds, pressure bonds, microwave bonds, mechanical entanglement, hydroentanglement, or any other conventional technique.

In an embodiment, the contact member 52 can have a bonded edge 56, which can be bonded to the cover 34, and a free edge 58. It is to be understood that while edge 56 is described herein as a bonded edge, in an embodiment, both edges, 56 and 58, of the contact member can be free edges and the bonding of the contact member 52 to the cover 34 can occur at any location of the contact member 52 between the two edges, 56 and 58, as desired. It is to be understood that while the edges, 56 and 58, are illustrated in the various figures described herein as straight lines, it is to be understood that the edges, 56 and 58, can be linear, non-linear, arcuate, and any combination thereof deemed suitable. In an embodiment, the bonded edge 56 can have a length 60 which can be any length deemed suitable to bond the contact member 52 to the cover 34. In an embodiment, the length 60 can be at least about 1 mm. In an embodiment, the length 60 can be at least about 1, 2, 3, 4, or 5 mm. In an embodiment, the length 60 can be from about 1, 2, 3, 4, or 5 mm to about 6, 7, 8, 9, or 10 mm. The bonding of the contact member 52 to the cover 34 can be continuous or intermittent. The bonding of the contact member 52 to the cover 34 can occur across the full width 122 of the cover 34 or any amount less than the full width 122 of the cover 34. It is to be understood that the contact member 52 can be bonded to the cover 34 in any manner as deemed suitable. In an embodiment, the contact member 52 can be located between the cover 34 and the body facing surface 36 of a resultant absorbent core 26 of a pledget 12. In such an embodiment, the cover 34 can be slit or offset from the contact element(s) 54 so as to allow the contact element(s) 54 to deform and flex away from the absorbent core 26 of the pledget 12. In an embodiment, the contact member 52 can be separated from the body facing surface 36 of a resultant absorbent core 26 of a pledget 12 by a cover 34 such that the contact member 52 and the contact element(s) 54 can directly contact the walls of the vaginal cavity.

In an embodiment, the contact member 52 can have at least one contact element 54. In an embodiment, the contact member 52 can have at least 1, 2, 3, 4, 5, 6, 7, 8, 9, or 10 contact elements 54. In an embodiment, the contact member 52 can have from 1, 2, 3, 4, 5, 6, 7, 8, 9, or 10 to 11, 12, 13, 14, 15, 16, 17, 18, 19, or 20 contact elements 54.

In an embodiment, a contact element 54 can be at least partially separated from another contact element 54 by a slit 62. The slit 62 can be cut through the material of the contact member 52 and can extend from a first surface 64 of the contact member 52 through to a second surface 66 of the contact member 52. In an embodiment, the slit 62 can extend from the free edge 58 of the contact member 52 toward the bonded edge 56 of the contact member 52. In various embodiments, the slit 62 can extend in a straight line, an arcuate line, or combinations thereof, from the free edge 58 of the contact member 52 towards the bonded edge 56 of the contact member 52. In an embodiment, the slit 62 can extend any length 68 as desired from the free edge 58 of the contact member 52 toward the bonded edge 56 of the contact member 52. It is to be understood that the slit 62 does not have to extend from the free edge 58 of the contact member 52. It is to be understood that the slit 62 can be located in any location of the contact member 52 as deemed suitable. The length 68 can be measured as the length 68 between the terminal ends of the slit 62. In an embodiment in which the slit 62 contains an arc, the arc length can be determined by any manner deemed suitable by one of ordinary skill in determining the length 68 of the slit 62. In various embodiments, the slit length 68 can be equal to, less than, or greater than the length 82 of the contact member 52 between the free edge 58 and the bonded edge 56. As a non-limiting example, in an embodiment, the slit length 68 can be a length 68 longer than the length 82 between the free edge 58 and the bonded edge 56 of the contact member 52 as can occur when the slit 62 is cut at an angle to the free edge 58 or when the slit 62 contains an arc. In an embodiment in which the slit 62 is cut at an angle to the free edge 58, the slit length 68 can be longer than the length 82 between the free edge 58 and the bonded edge 56 of the contact member 52, however, the projected length can be as long as the length 82 between the free edge 58 and the bonded edge 56 of the contact member 52. In an embodiment, the slit length 68 can range from about 1, 2, 3, 4, 5, 6, 7, 8, 9, 10, 11, 12, 13, 14 or 15 mm to about 16, 17, 18, 19, 20, 21, 22, 23, 24, 25, 26, 27, 28, 29 or 30 mm. In an embodiment, the slit length 68 can be greater than about 1, 2, 3, 4, 5, 6, 7, 8, 9, 10, 11, 12, 13, 14 or 15 mm.

As noted above, in an embodiment, a contact member 52 can have an edge, such as edge 56 or 58, which can be linear, non-linear, arcuate, and any combination thereof as deemed suitable. Such an edge can be produced in any manner as deemed suitable, such as, but not limited to, knife cutting, die cutting, or any other method known to one skilled in the art. In an embodiment, the contact member 52 can have an edge, such as edge 56 or 58, which can be arcuate. In such an embodiment, a contact member 52 edge, 56 or 58, can have an undulating arcuate pattern that can produce discrete contact elements 54. The amplitude of each arc can be any amplitude as deemed suitable. In such an embodiment, a contact element 54 can, therefore, be at least partially separated from another contact element 54 by the amplitude of the arc. It should be understood that in such an embodiment, a slit 62 need not be present to form a contact element 54. In such an embodiment, a slit 62 can be used in combination with the amplitude of an arc to separate one contact element 54 from another contact element 54.

In an embodiment, the contact member 52 can have three regions: a slit region 70, a bonded region 72, and a free non-slit region 74. The slit region 70 can be the portion of the contact member 52 containing the slit(s) 62. The bonded region 72 can be the portion of the contact member 52 containing the bonded edge 56 of the contact member 52. The free non-slit region 74 can be the portion of the contact member 52 which is not bonded to the cover 34 and does not contain any slit(s) 62. In an embodiment, the contact member 52 can have a slit region 70 having a length 76 from about 1, 2, 3, 4, 5, 6, or 7 mm to about 8, 9, 10, 11, 12, 13, 14, or 15 mm, a bonded region 72 having a length 78 from about 1, 2, 3, 4, or 5 mm to about 6, 7, 8, 9, or 10 mm, and a free non-slit region 74 having a length 80 from about 1, 2, 3, 4, or 5 mm to about 6, 7, 8, 9, or 10 mm. In an embodiment, a contact member 52 can have multiple bonded regions 72, multiple slit regions 70, multiple free non-slit regions 74, and combinations thereof.

In an embodiment, the contact member 52 can have at least one slit 62. In an embodiment, the contact member 52 can have at least 1, 2, 3, 4, 5, 6, 7, 8, 9, or 10 slits 62. In an embodiment, the contact member 52 can have from about 1, 2, 3, 4, 5, 6, 7, 8, 9, or 10 to about 11, 12, 13, 14, 15, 16, 17, 18, 19, or 20 slits 62. In an embodiment, the contact member 52 has the appropriate number of slits 62 to provide the desired number of contact elements 54.

In an embodiment in which the contact member 52 has more than one slit 62, each slit can have the same length 68. In an embodiment in which the contact member 52 has more than one slit 62, a slit 62 can have a length 68 that differs from the length 68 of at least one other slit 62. In an embodiment, at least about 20, 25, 40, 45, 50, 55, 70, 75, 80 or 85% of the slits 62 of the contact member 52 can have substantially the same length 68. In an embodiment, about 50% of the slits can have substantially the same length (e.g., a first length) and about 50% of the slits can have substantially the same length (e.g., a second length) and the second length can be different from the first length. In such an embodiment, each successive slit 62 on the contact member 52 can be of an alternating length or any other pattern of lengths as deemed suitable. In an embodiment in which multiple slits 62 are present, any width 84 as deemed suitable may separate one slit 62 from the next successive slit 62. Such width 84 can be recognized as a width 84 of a contact element 54. In an embodiment, the width 84 may range from about 1, 2, 3, 4, 5, 6 or 7 mm to about 8, 9, 10, 11, 12, 13, 14, or 15 mm.

In an embodiment, the slit(s) 62 can be incorporated into the contact member 52 when the contact member 52 is in a flat, unfolded configuration or when the contact member 52 is in a folded configuration. In an embodiment, the slit 62 can be a cut in the contact member 52 which fully extend from a first surface 64 through to a second surface 66 of a contact member 52. In an embodiment, the slit 62 can be a continuous or intermittent cut. In an embodiment, the slit 62 can be a line of weakness. In an embodiment, the slit 62 can be linear, arcuate, or combinations thereof.

Figure 9A:
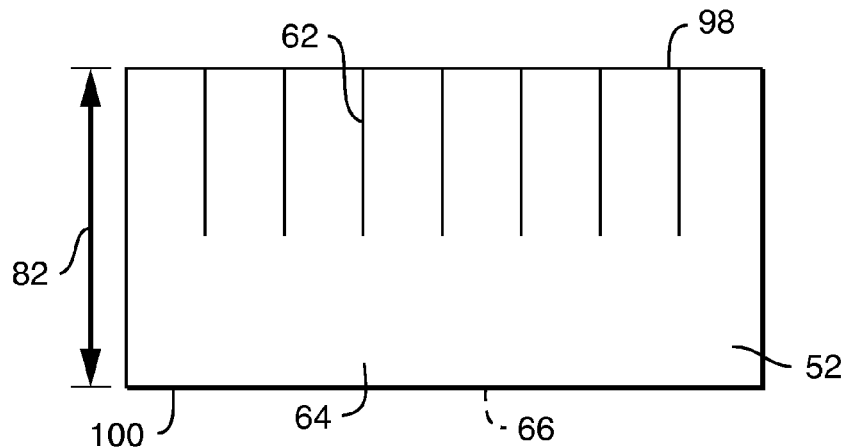
FIG. 9A-9E are top views of slits incorporated into a contact member in a flat, unfolded configuration.
Figure 9B:
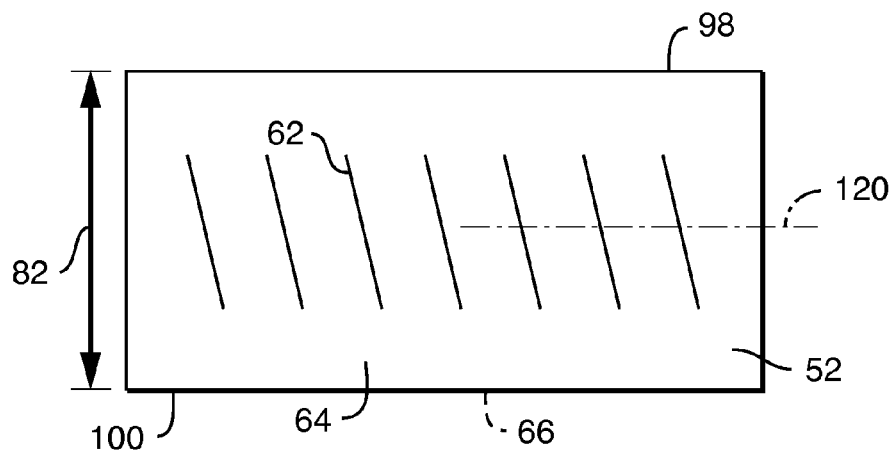
Figure 9C:
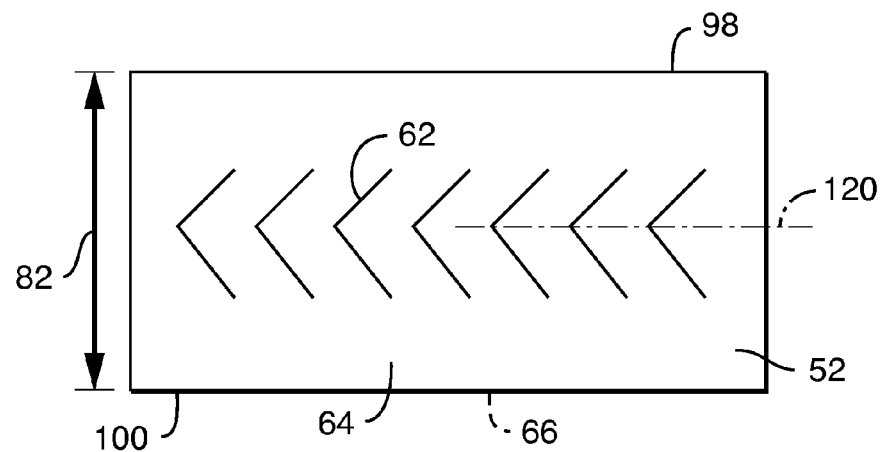
Figure 9D:
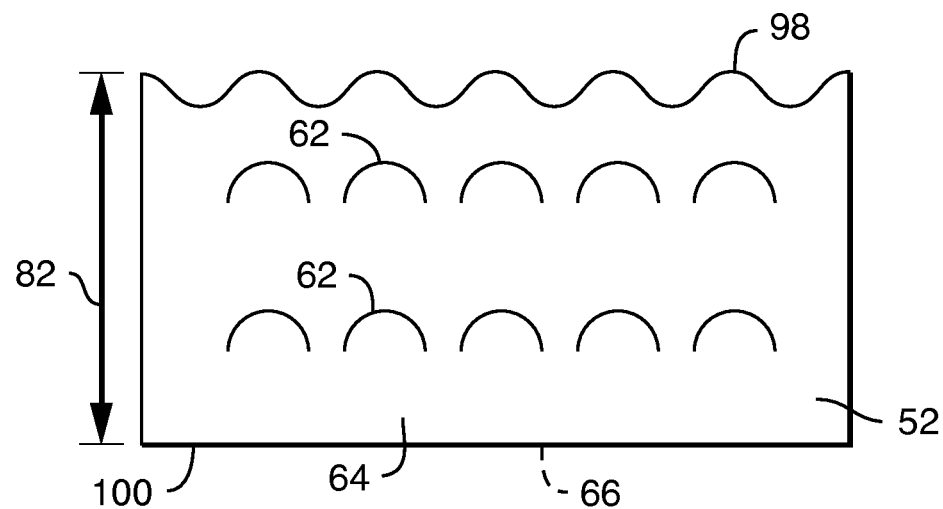
Figure 9E:
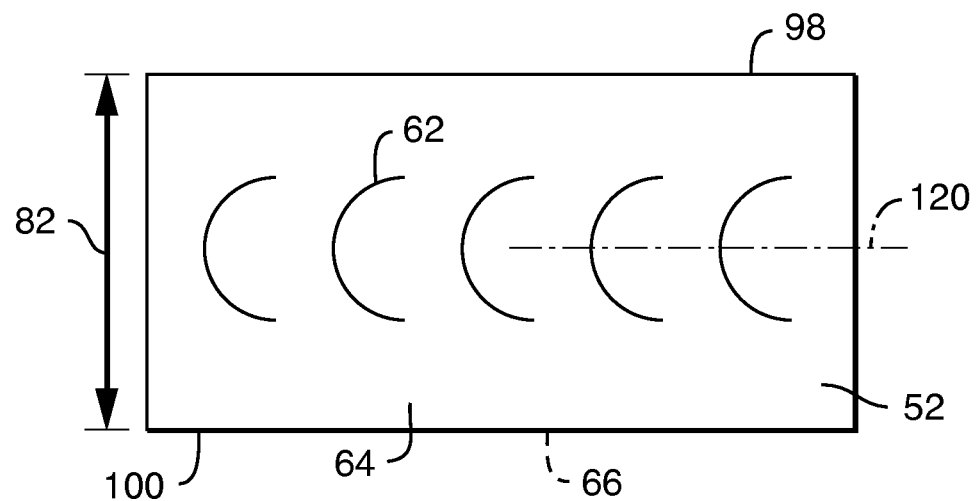

FIG. 9A-9E illustrate various embodiments of slits 62 incorporated into the contact member 52. As shown in the non-limiting examples of FIG. 9A-9E, the slits 62 can be cut through from a first surface 64 to a second surface 66 of a contact member 52. FIG. 9A provides a non-limiting example of slits 62 extending from a first edge 98 of contact member 52 towards a second edge 100 of contact member 52. As shown in FIG. 9A, the slits 62 do not extend the entire length 82 of the contact member 52. Additionally, as illustrated in FIG. 9A, the slits 62 are cut to extend in a straight line from the first edge 98 towards the second edge 100 of the contact member 52. FIG. 9B provides a non-limiting example of slits 62 incorporated into the contact member 52 and positioned along a centerline 120 of the contact member 52. The contact member 52 may be folded during manufacturing, as will be described herein, and a fold 86 can be formed along the centerline 120 of the contact member 52. After the folding of the contact member 52, a slit 62 can have two sides oriented in opposite directions from each other. FIG. 9C provides a non-limiting example of slits 62 incorporated into a contact member 52 along a centerline 120 of the contact member 52. The slits 62 are illustrated in a chevron pattern. The contact member 52 can be folded during manufacturing and a fold 86 can be formed along the centerline 120 of the contact member 52. After the folding of the contact member 52, a slit 62 can have two sides oriented in the same direction as each other. FIG. 9D provides a non-limiting example of slits 62 incorporated into a contact member 52 wherein the slits 62 are provided in an arcuate manner. In such an embodiment, the contact member 52 can be manipulated into a folded configuration such as described herein, however, it is to be understood that folding is not necessary. As further illustrated in FIG. 9D in a non-limiting example, at least one row of slit(s) 62 can be provided and in an embodiment, more than one row of slit(s) 62 can be provided. FIG. 9D further provides a non-limiting example of an edge 98 of the contact member 52 which can be formed with an undulating arcuate pattern. FIG. 9E provides a non-limiting example of slits 62 incorporated into a contact member 52 along a centerline 120 of the contact member 52. The slits 62 are illustrated in an arcuate manner. The contact member 52 can be folded during manufacturing and a fold 86 can be formed along the centerline 120 of the contact member 52. After the folding of the contact member 52, a slit 62 can have two sides oriented in the same direction as each other. While the illustrations of FIG. 9A-9E generally illustrate patterns of slit(s) 62, it is to be understood that the slit(s) 62 can be symmetrical, asymmetrical, arcuate, or any other configuration as deemed suitable. While the illustrations of FIGS. 9B, 9C, and 9E generally illustrate a centerline 120 that will produce symmetrical sides of the contact member 52 around a fold 86, it is to be understood that the fold 86 need not always be positioned at a centerline 120 of the contact member 52. It may be deemed suitable to place a fold, such as fold 86, offset from the centerline 120 of the contact member 52. In such an embodiment, one side of a folded contact member 52 may be longer than the other side of the folded contact member 52.

Figure 10A:
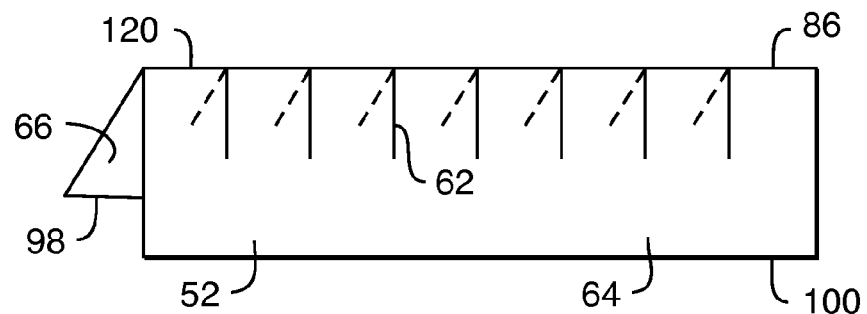
FIG. 10A-10C are perspective views of slits incorporated into a contact member in a folded configuration.
Figure 10B:
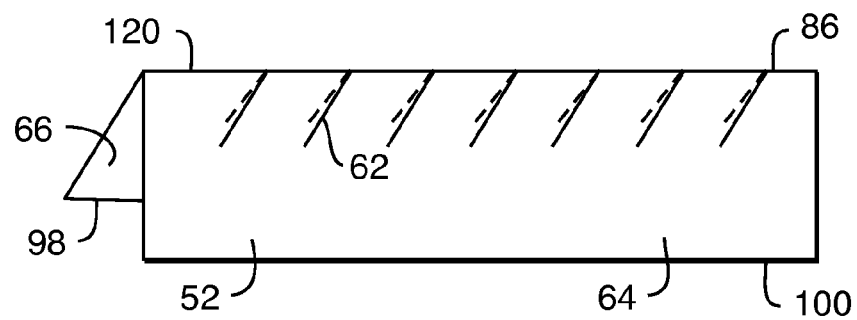
Figure 10C:
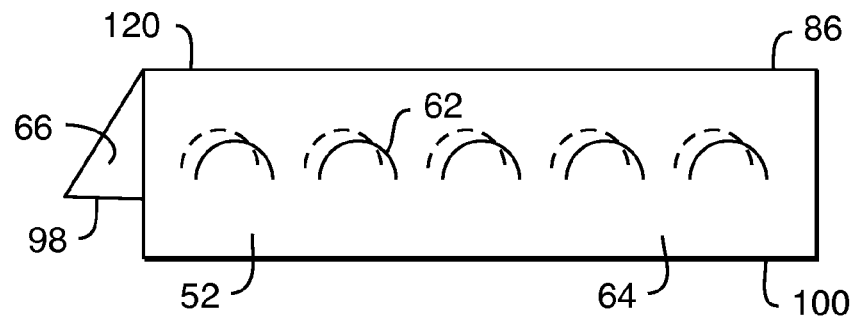

FIG. 10A-10C illustrate various embodiments of slits 62 incorporated into a contact member 52 when the contact member 52 is in a folded configuration. As shown in the non-limiting examples of FIG. 10A-10C, the slits 62 can be cut through from a first surface 64, through the second surface 66 and to the opposite first surface 64 of the contact member 52. FIG. 10A provides a non-limiting example of slits 62 extending from a fold 86 in a direction towards the first and second edges, 98 and 100, of the contact member 52. As shown in FIG. 10A, the slits 62 do not extend the entire length of the contact member 52. Additionally, as illustrated in FIG. 10A, the slits 62 are cut to extend in a straight line from the fold 86 towards the first and second edges, 98 and 100, of the contact member 52. FIG. 10B provides a non-limiting example of slits incorporated into a folded contact member 52. The slits 62 are illustrated as extending at an angle from the fold 86 towards the first and second edges, 98 and 100, of the contact member 52. FIG. 10C provides a non-limiting example of slits 62 provided in an arcuate configuration. As illustrated, the slits 62 do not extend from the fold 86 of the contact member 52.

A slit can have a directional relationship with the longitudinal axis 16 of a resultant absorbent core 26 of a pledget 12. In an embodiment, a slit 62 may be incorporated into the contact member 52 in a direction parallel to the longitudinal axis 16 of the resultant absorbent core 26 of a pledget 12. In an embodiment, a slit 62 may be incorporated into the contact member 52 in a direction perpendicular to the longitudinal axis 16 of the resultant absorbent core 26 of a pledget 12. In an embodiment, a slit 62 can be incorporated into the contact member 52 in a direction at an angle to the longitudinal axis 16 of the resultant absorbent core 26 of a pledget 12. As noted above, a slit 62 can be incorporated in the contact member 52 in an arcuate configuration.

In an embodiment, a contact element 54 can have a directional relationship with the longitudinal axis 16 of the resultant absorbent core 26 that is substantially similar to the relationship of a slit 62 to the longitudinal axis 16 of the resultant absorbent core 26 of the pledget 12. In an embodiment, a contact element 54 of a contact member 52 can be parallel with the longitudinal axis 16 of the resultant absorbent core 26 of the pledget 12. In an embodiment, a contact element 54 of a contact member 52 can be perpendicular to the longitudinal axis 16 of the resultant absorbent core 26 of the pledget 12. In an embodiment, a contact element 54 of a contact member 52 can be at an angle to the longitudinal axis 16 of the resultant absorbent core 26 of the pledget 12. In an embodiment in which a slit 62 can be provided in an arcuate configuration, a contact element 54 can have any relationship with the longitudinal axis 16 of the resultant absorbent core 26 of the pledget 12 as desired.

In an embodiment, the contact member 52 can be aligned on the cover 34 such that the bonded edge 56 of the contact member 52 can be parallel with the longitudinal axis 16 of the resultant absorbent core 26 of the pledget 12. In an embodiment, the contact member 52 can be aligned on the cover 34 such that the bonded edge 56 of the contact member 52 is perpendicular to the longitudinal axis 16 of the resultant absorbent core 26 of the pledget 12. In an embodiment, the contact member 52 can be aligned on the cover 34 such that the bonded edge 56 of the contact member 52 can be at an angle to the longitudinal axis 16 of the resultant absorbent core 26 of the pledget 12. In such an embodiment, the contact member 52 may be configured to spiral around the resultant absorbent core 26 of the pledget 12.

Figure 11:
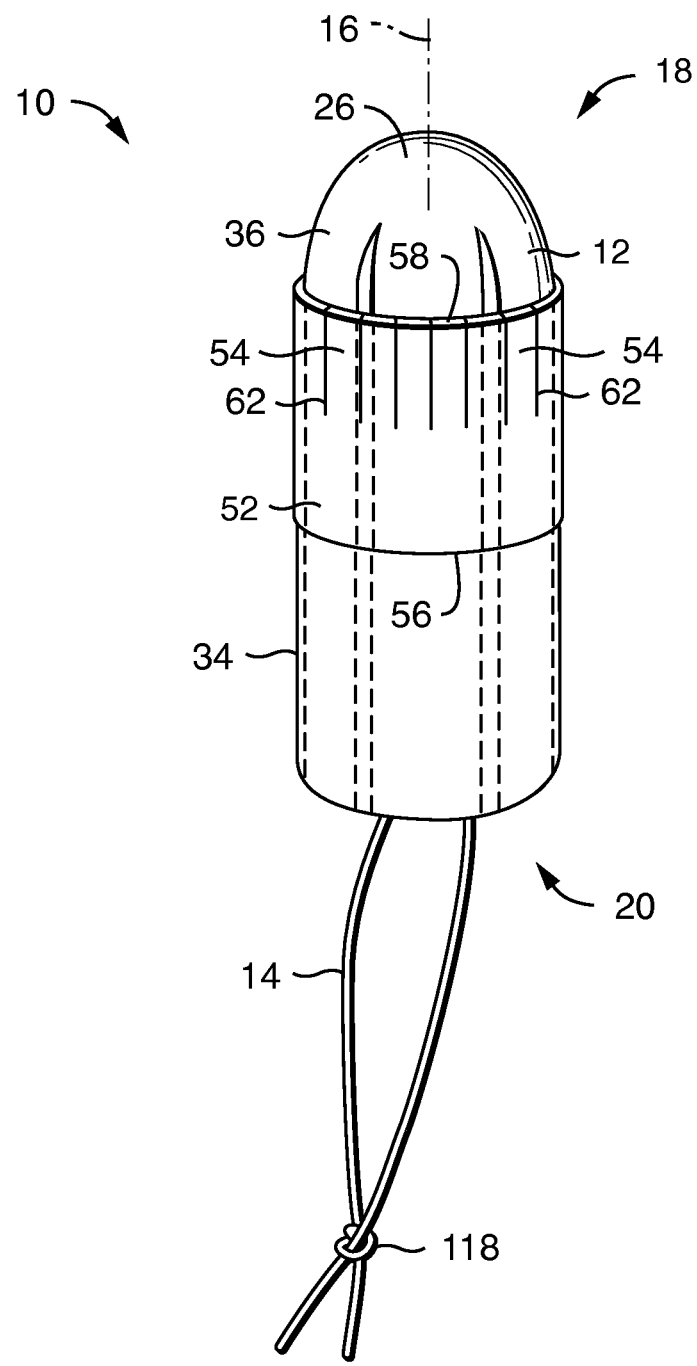
FIG. 11 is a perspective view of an embodiment of a tampon.
Figure 12:
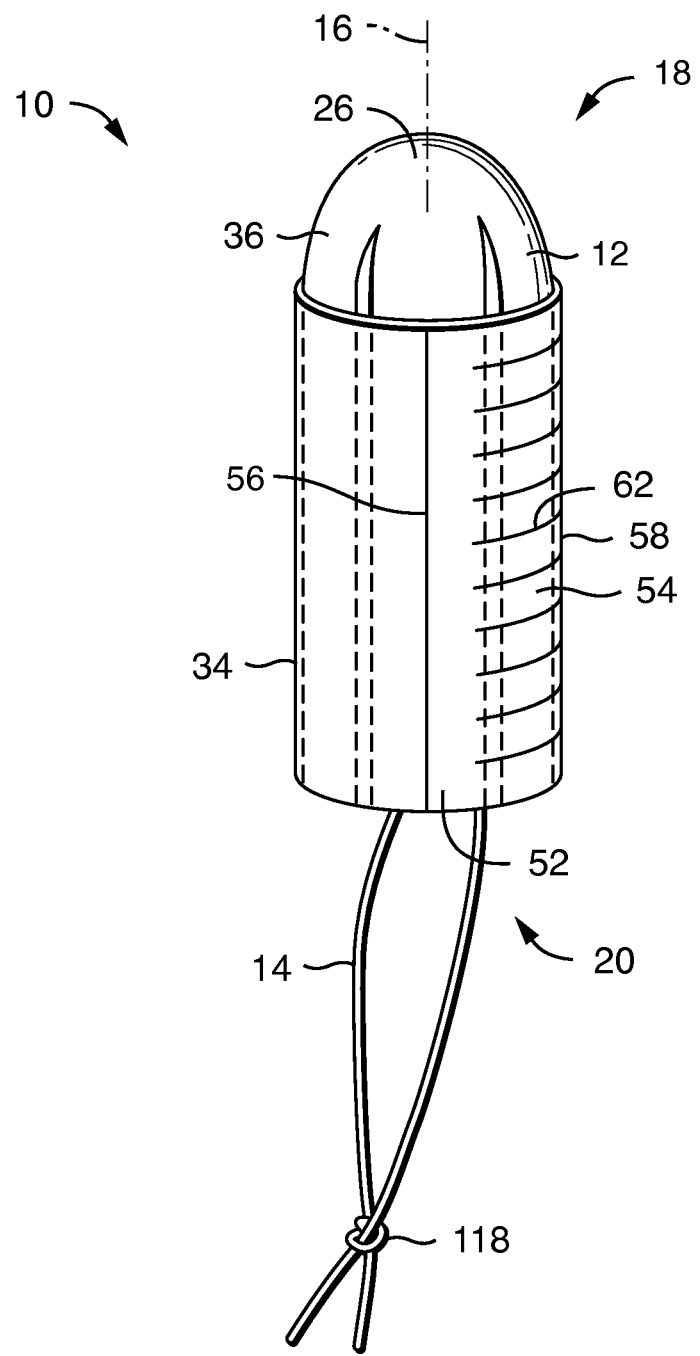
FIG. 12 is a perspective view of an embodiment of a tampon.
Figure 13:
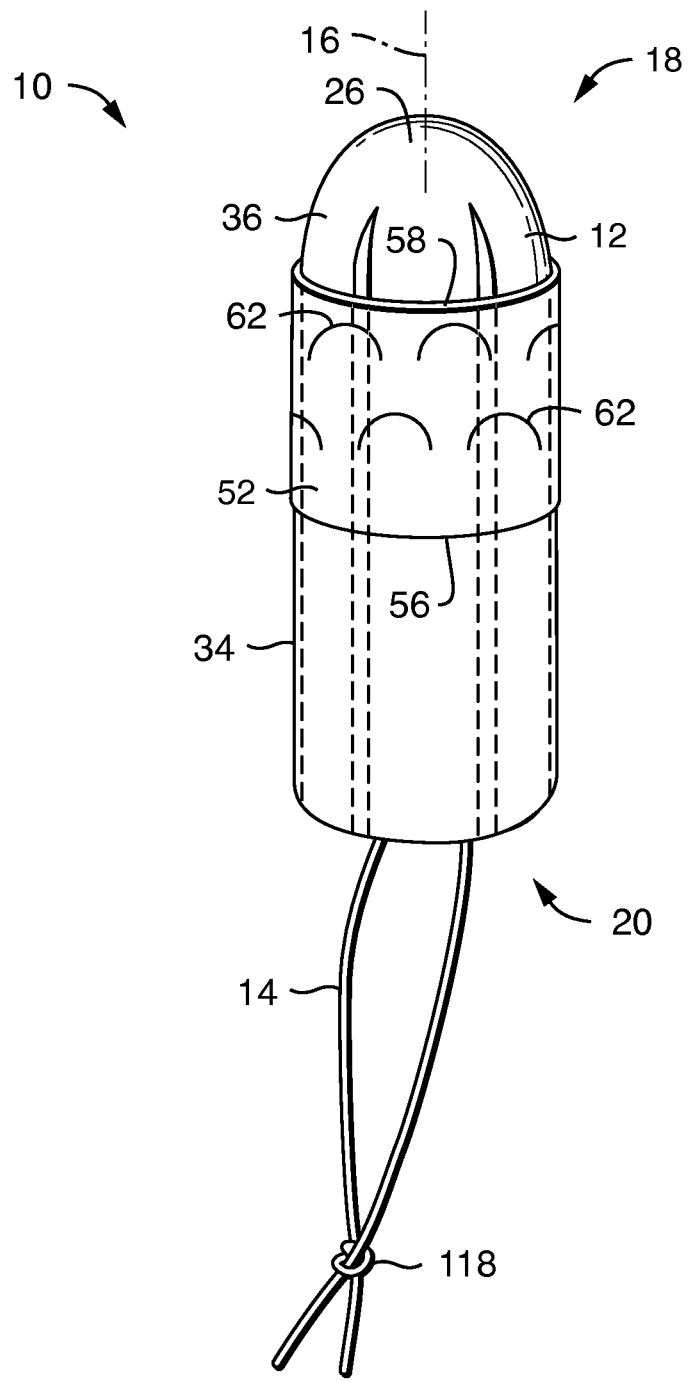
FIG. 13 is a perspective view of an embodiment of a tampon.

FIGS. 11 through 13 provide non-limiting illustrations of exemplary embodiments of an absorbent core 26 of a pledget 12 of a tampon 10. In the non-limiting illustration shown in FIG. 11, the slits 62 and the contact elements 54 of the contact member 52 are in a direction parallel to the longitudinal axis 16 of the absorbent core 26 of the pledget 12. In such an embodiment, the bonded edge 56 can be perpendicular to the longitudinal axis 16 of the absorbent core 26 of the pledget 12. In the non-limiting illustration shown in FIG. 12, the slits 62 and the contact elements 54 of the contact member 52 are in a direction perpendicular to the longitudinal axis 16 of the absorbent core 26 of the pledget 12. In such an embodiment, the bonded edge 56 can be parallel to the longitudinal axis 16 of the absorbent core 26 of the pledget 12. In the non-limiting illustration shown in FIG. 13, the slits 62 are provided in an arcuate configuration and the contact elements 54 of the contact member 52 are in a direction parallel to the longitudinal axis 16 of the absorbent core 26 of the pledget 12. In the embodiment illustrated, the bonded edge 56 can be perpendicular to the longitudinal axis 16 of the absorbent core 26 of the pledget 12.

In an embodiment, the contact member 52 can be bonded to the cover 34 in any location of the cover 34 as deemed suitable. In an embodiment, the bonded edge 56 of the contact member 52 can be substantially aligned with an edge, such as edges 42 or 44, of the cover 34. In an embodiment in which the bonded edge 56 is perpendicular to the longitudinal axis 16 of the absorbent core 26, the bonded edge 56 of the contact member 52 can be positioned at any location along the longitudinal axis 16 of the absorbent core 26 as deemed suitable. In an embodiment, the free edge 58 of the contact member 52 can be substantially aligned with an edge, such as edge 42 or 44, of the cover 34. In an embodiment, the free edge 58 of the contact member 52 can extend beyond an edge, 42 or 44, of the cover 34. In an embodiment, the free edge 58 of the contact member 52 can extend beyond the insertion end 18 or the withdrawal end 20 of the pledget 12 of the tampon 10. It is to be understood that the contact member 52 can extend beyond an edge, 42 or 44, of the cover 34, beyond the insertion end 18, beyond the withdrawal end 20 of the pledget 12 of the tampon 10 in any configuration such as when the contact member 52 is parallel to, perpendicular to, or at an angle to the longitudinal axis 16 of the absorbent core 26 of the pledget 12 of the tampon 10.

Figure 14:
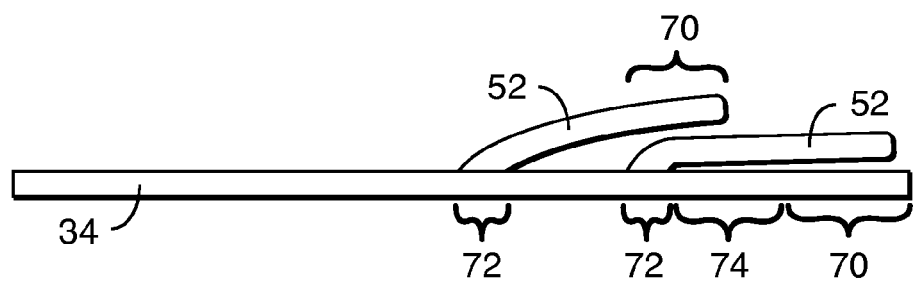
FIG. 14 is a side view of an embodiment of two contact members in communication with a cover.

In an embodiment, at least one contact member 52 is bonded with the cover 34. In an embodiment, at least 1, 2, 3, 4, or 5 contact members 52 can be bonded with the cover 34. In an embodiment, the cover 34 can be bonded to from 1, 2, 3, 4, or 5, to 6, 7, 8, 9, or 10 contact members 52. In an embodiment in which multiple contact members 52 are present, a contact member 52 can be bonded to the cover 34, one or more additional contact members 52, itself, or combinations thereof. In an embodiment in which multiple contact members 52 are present, a portion of a contact member 52 can overlap a portion of another contact member 52. For example, a slit region 70 of one contact member 52 can overlap a bonded region 72, a free non-slit region 74, a slit region 70, or combinations thereof of another contact member 52. FIG. 14 provides a non-limiting illustration of a cover 34 in communication with two contact members 52 in which a slit region 70 of a first contact member 52 can overlap a bonded region 72 and a portion of a free non-slit region 74 of a second contact member 52. In an embodiment, in which multiple contact members 52 are present, the contact members 52 can be oriented in the same direction (e.g., the free edges 58 of each contact member 52 are oriented towards the insertion end 18), in opposite directions (e.g., a free edge 58 of one contact member 52 is oriented towards the insertion end 18 and a free edge 58 of a different contact member 52 is oriented towards the withdrawal end 20), and combinations thereof.

Figure 15A:
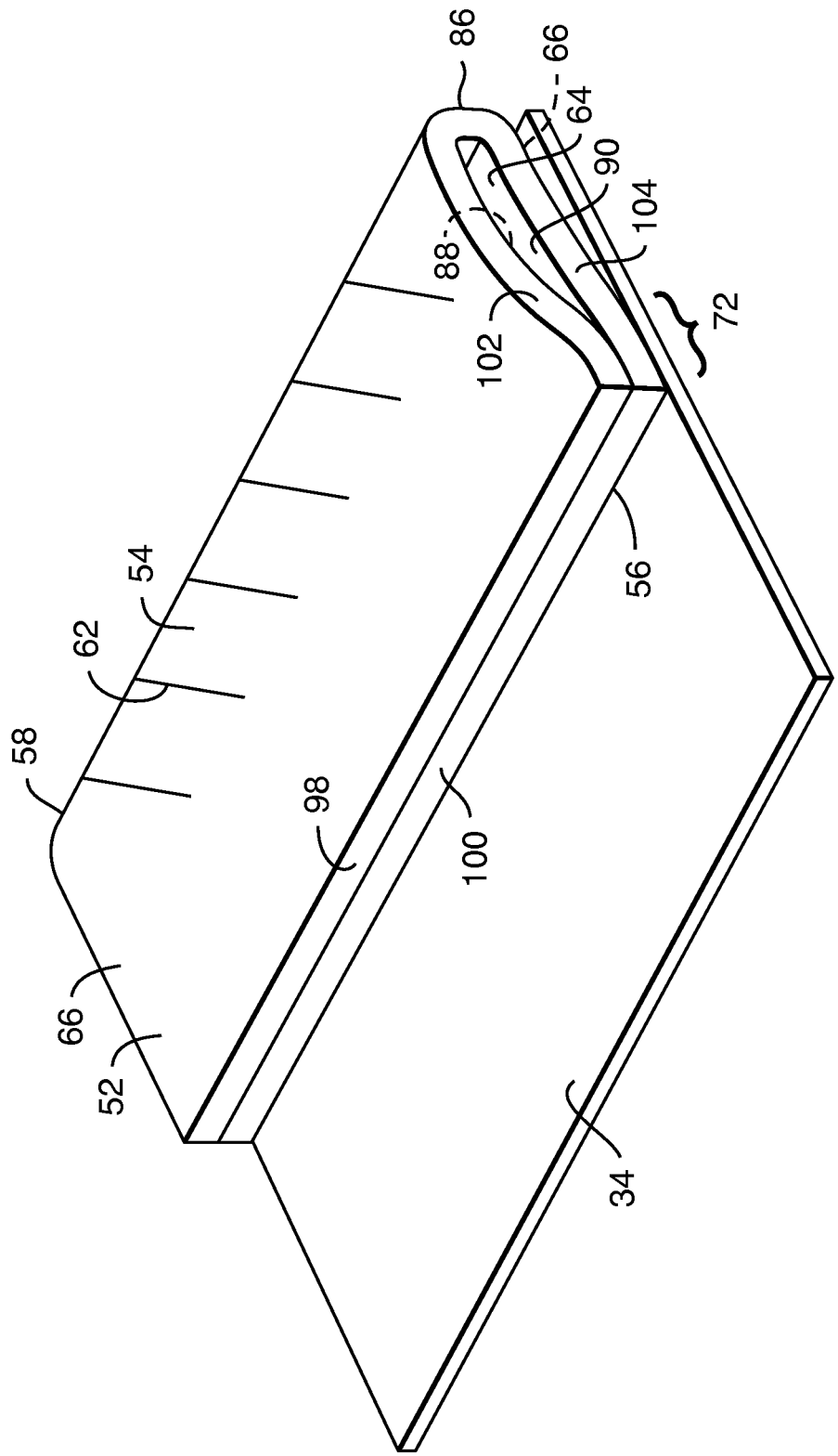
FIG. 15A is a perspective view of an embodiment of a contact member with a single fold and in communication with a cover.
Figure 15B:
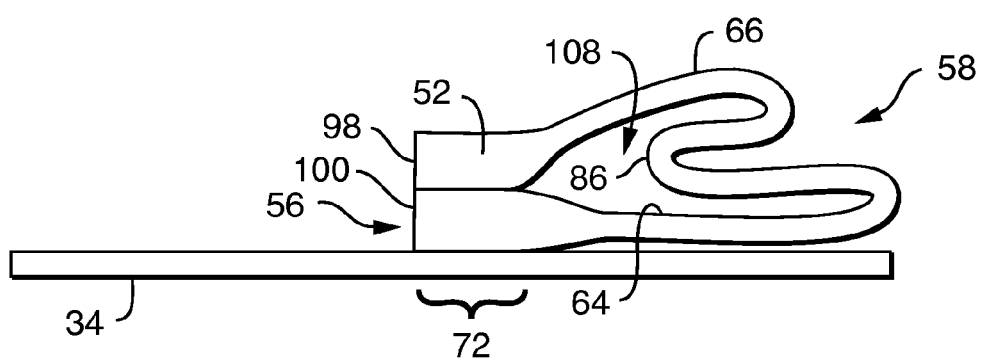
FIG. 15B is a side view of an embodiment of a contact member with a fold and in communication with a cover.

As illustrated in FIG. 15A, in an embodiment, the contact member 52 can have at least one fold 86. In such an embodiment in which a fold 86 is present, the contact member 52 can be bent upon itself such that one surface, 64 or 66, associated with the first edge 98 of the contact member 52 can be in communication with the same surface, 64 or 66, associated with the second edge 100 of the contact member 52. As a non-limiting example, as illustrated in FIG. 15A, the contact member 52 can contain a single fold 86 bringing a first portion 88 of the first surface 64 into communication with a second portion 90 of the first surface 64. In the example illustrated in FIG. 15A, the fold 86 can bring a first edge 98 of the contact member 52 into communication with a second edge 100 of the contact member 52. In an embodiment, when such a contact member 52 is bonded to a cover 34, the two edges, 98 and 100, can be contained within the bonded region 72 and the fold 86 can be a free edge 58 of the contact member 52. As discussed above, the contact member 52 can have at least one slit 62 extending through the layers, 102 and 104, of the contact member 52. As discussed above, in an embodiment, the slit 62 can extend from the free edge 58 (i.e., the fold 86) of the contact member 52 in a direction toward the bonded region 72 of the contact member 52. The at least one slit 62 can be incorporated into the contact member 52 prior to or after the contact member 52 has been folded. As illustrated in FIG. 15B, in an embodiment, the contact member 52 can have at least one fold 86 which can be positioned inward of the contact member 52 such that the fold 86 can be positioned in the interior region 108 of the contact member 52. In such an embodiment, multiple layers of contact elements 54 can overlap each other.

Figure 16:
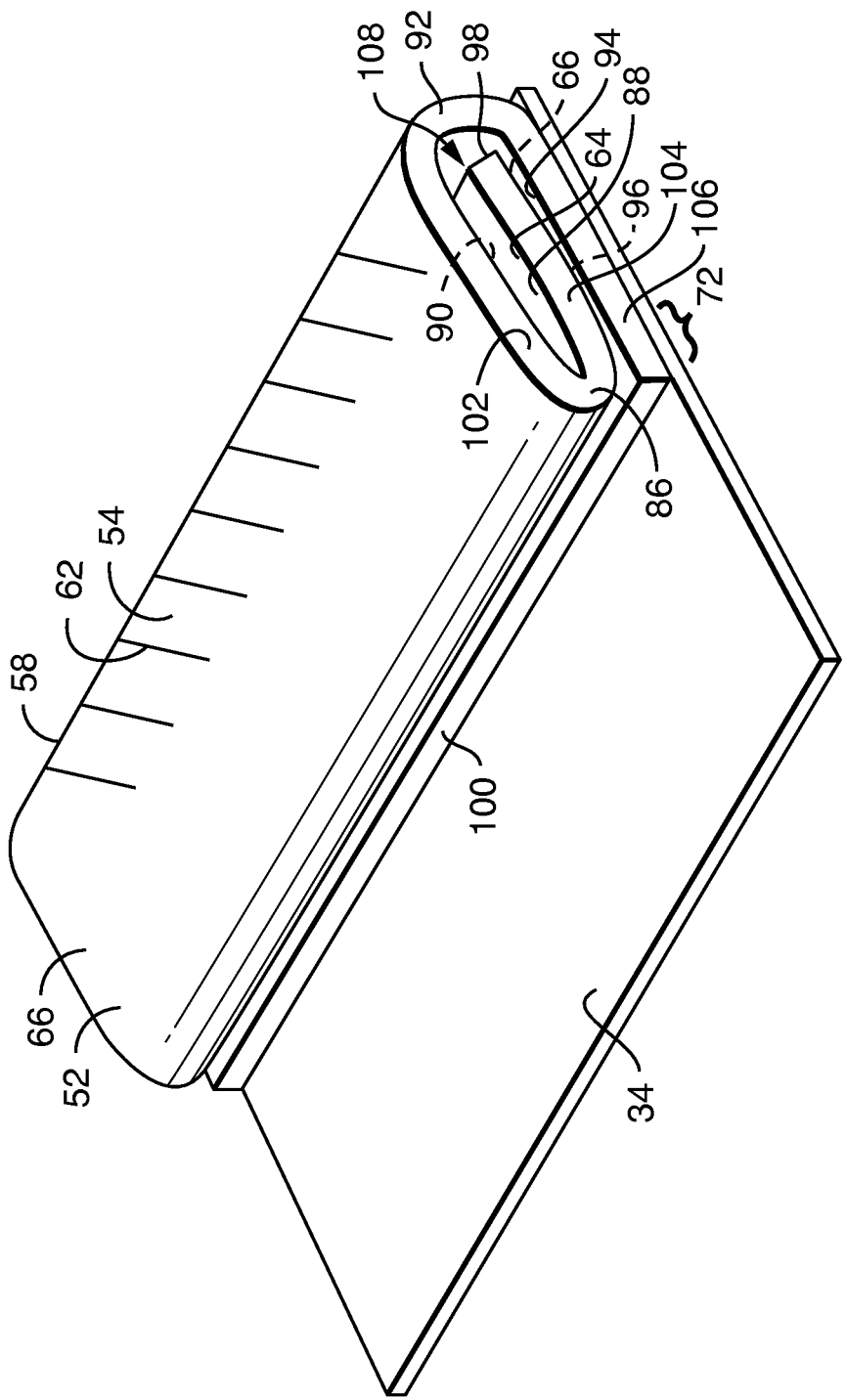
FIG. 16 is a perspective view of an embodiment of a contact member with two folds and in communication with a cover.

As illustrated in FIG. 16, in an embodiment, the contact member 52 can have at least two folds 86 and 92. In such an embodiment in which two folds 86 and 92 are present, the contact member 52 can be bent upon itself such that a first portion of one surface, 64 or 66, of the contact member 52 can be in communication with a second portion of the same surface, 64 or 66, and a third portion of one surface, 64 or 66, of the contact member 52 can be in communication with a portion of the other surface, 64 or 66. As a non-limiting example, as illustrated in FIG. 16, the contact member 52 can contain a first fold 86 bringing a first portion 88 of the first surface 64 into communication with a second portion 90 of the first surface 64. The contact member 52 can contain a second fold 92 bringing a third portion 94 of the first surface 64 into communication with a first portion 96 of the second surface 66. In the example illustrated in FIG. 16, the fold 86 can bring a first edge 98 of the contact member 52 into communication with an interior region 108 of the contact member 52 and the fold 92 can bring a second edge 100 of the contact member 52 into communication with the first fold 86. In an embodiment, when such a contact member 52 is bonded to a cover 34, the first fold 86 and the second edge 100 can be contained within the bonded region 72 and the second fold 92 can be a free edge 58 of the contact member 52. In an embodiment, the contact member 52 can have at least one slit 62 extending through the layers, 102, 104 and 106, of the contact member 52 and extending from the free edge 58 (i.e., the fold 92) of the contact member 52 in a direction toward the bonded region 72 of the contact member 52. The at least one slit 62 can be incorporated into the contact member 52 prior to or after the contact member 52 has been folded.

FIG. 17 is an illustration of a non-limiting example of a contact member 52 which can be in communication with an outer sheath 110. In various embodiments, the outer sheath 110 can be formed from nonwoven materials or apertured films. The nonwoven materials can include, but are not limited to, materials such as natural fibers, synthetic fibers, or blends of natural and synthetic fibers. Natural fibers include, but are not limited to, rayon, cotton, wood pulp, flax, and hemp. Synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. The outer sheath 110 can be made by any number of suitable techniques such as, for example, being spunbond, carded, hydroentangled, thermally bonded, and resin bonded. In an embodiment, the outer sheath 110 can be formed from an apertured thermoplastic film having either a two-dimensional or a three-dimensional thickness. In an embodiment, the outer sheath 110 can be a 12 gsm smooth calendared material made from bicomponent, polyester sheath and polyethylene core, fibers such as Sawabond 4189 available from Sandler AG, Schwarzenbach, Germany. In an embodiment, the outer sheath 110 can be formed from a single piece of material. In an embodiment, the outer sheath 110 can be formed from multiple discrete pieces of material which are bonded together.

Figure 18:
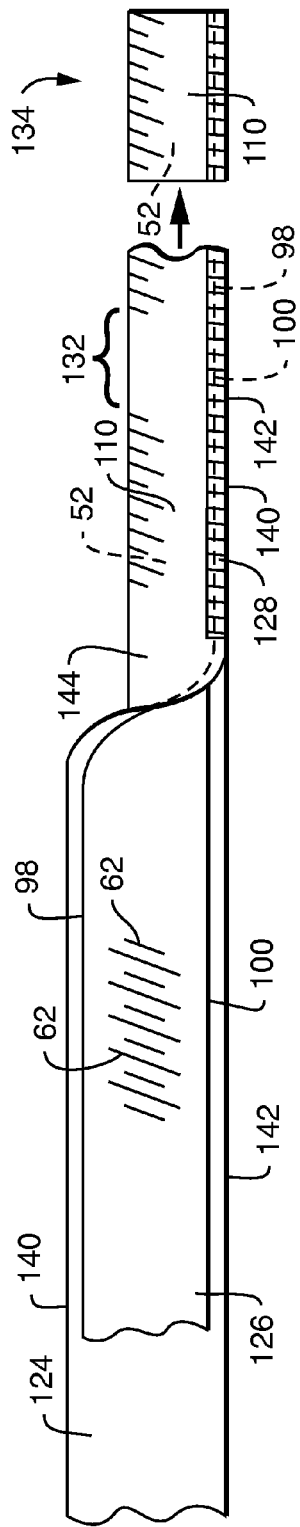
FIG. 18 is a perspective view of an embodiment of a method of bonding an outer sheath to a contact member.

In an embodiment in which the contact member 52 is in communication with an outer sheath 110, the outer sheath 110 can be bonded to the contact member 52 in any manner such that the outer sheath 110 encloses the contact member 52. For example, FIG. 18 illustrates an embodiment of a method of bonding an outer sheath 110 to a contact member 52. FIG. 18 illustrates an outer sheath ribbon 124 in contact with a contact member ribbon 126. The contact between the outer sheath ribbon 124 and the contact member ribbon 126 can be enhanced by bonding the two ribbons, 124 and 126, together by any method including, but not limited to, adhesives, thermal bonding, pressure bonding, mechanical entanglement, hydroentanglement, ultrasonic bonds, microwave bonds, or any other conventional technique. The contact member ribbon 126 and the outer sheath ribbon 124 can each be provided with at least one slit 62 in an area where the two ribbons, 124 and 126, overlap. The incorporation of the at least one slit 62 can be completed by any manner deemed suitable such as, for example, knife cutting. The contact member ribbon 126 and the outer sheath ribbon 124 can be folded either before or after the incorporation of the at least one slit 62. The outer sheath ribbon 124 can be folded over the contact member ribbon 126 to enclose the contact member ribbon 126 within the outer sheath ribbon 124. It is to be understood that the contact member ribbon 126 need not be folded and the at least one slit 62 can be incorporated into a folded or un-folded contact member ribbon 126. Folding the outer sheath ribbon 124, and the contact member ribbon 126 if desired, can bring the first edge 140 and the second edge 142 of the outer sheath ribbon 124 into communication with each other and the two edges, 140 and 142, can be bonded together in a bond area 128. In an embodiment in which the contact member ribbon 126 has also been folded, the edges, 98 and 100, of the contact member ribbon 126 can be brought into communication with each other as well as, in an embodiment, with the edges, 140 and 142, of the outer sheath ribbon 124 and can be bonded together in the bond area 128. Following the bonding of the edges, 140 and 142, of the outer sheath ribbon 124, a combination ribbon 144, having both a contact member ribbon 126 and an outer sheath ribbon 124 can be formed. The combination ribbon 144 can have multiple interconnected contact members 52 in communication with multiple interconnected outer sheaths 110. In an embodiment, the interconnected contact members 52 and outer sheaths 110 can be connected to each other in a continuous pattern in which substantially no discrete spacing exists between each combined contact member 52 and outer sheath 110. In an embodiment, the interconnected contact members 52 and outer sheaths 110 can be connected to each other in a discrete pattern in which an area 132 of the combination ribbon 144 exists between each contact member 52 and outer sheath 110 wherein the area 132 of the combined ribbon 144 does not contain at least one slit 62. The combined ribbon 144 can undergo a separation process, such as, but not limited to, knife cutting, wherein an individual discrete combination 134 of a contact member 52 having an outer sheath 110 is separated from the combined ribbon 144. The separation of the discrete contact member 52 and outer sheath 110 from the combined ribbon 144 can occur in any location along the combined ribbon 144 as desired such as, for example, in an area 132 in which the combined ribbon 144 does not contain at least one slit 62.

While FIG. 18 illustrates an embodiment of a method of bonding an outer sheath ribbon 124 and a contact member ribbon 126, it is to be understood that a discrete piece of outer sheath 110 material can be bonded to a discrete piece of contact member 52 material. In an embodiment, the outer sheath 110 can be bonded to the contact member 52 prior to or after the contact member 52 has been folded, if folding of the contact member 52 is desired. In an embodiment, the outer sheath 110 can enclose a contact member 52 that does not contain a fold 86. In an embodiment, the outer sheath 110 can be bonded to the contact member 52 prior to the incorporation of slit(s) 62 into the contact member 52. In such an embodiment, the outer sheath 110 and the contact member 52 can both be cut and provided with corresponding slit(s) 62. In an embodiment in which the contact member 52 is enclosed by an outer sheath 110, the outer sheath 110 can have a slit region 112, bonded region 114, and free non-slit region 116 corresponding to the slit region 70, bonded region 72, and free non-slit region 74, respectively, of the contact member 52.

Figure 19:
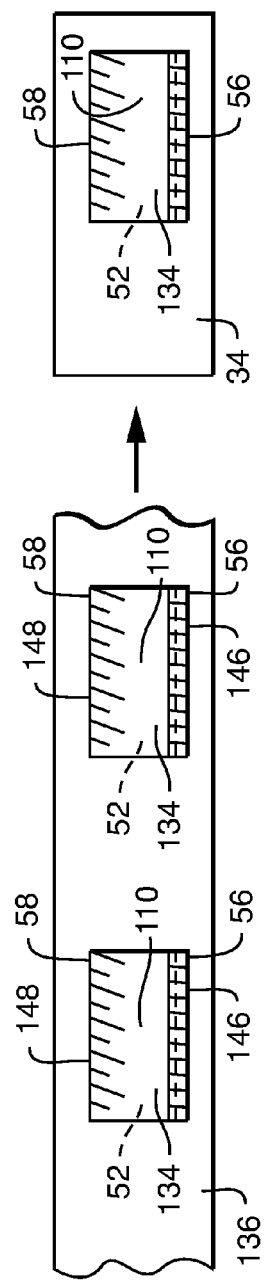
FIG. 19 is a perspective view of an embodiment of a method of bonding a contact member enclosed by an outer sheath to a cover.

In an embodiment, the combined ribbon 144 can be bonded to a cover ribbon 136. In an embodiment, a discrete contact member 52, and if desired a discrete outer sheath 110, can be bonded to a cover ribbon 136. In an embodiment, a discrete contact member 52, and if desired a discrete outer sheath 110, can be bonded to a discrete cover 34. FIG. 19 provides a non-limiting illustration of a method of bonding a discrete combination 134 of a contact member 52 and outer sheath 110 to a cover ribbon 136. As illustrated, a cover ribbon 136 can be provided and at least one discrete combination 134 of a contact member 52 and outer sheath 110 can be bonded to the cover ribbon 136. The discrete combination 134 of the contact member 52 and the outer sheath 110 can have a first edge, such as edge 146, which can be bonded to the cover ribbon 136 by any suitable method such as, but not limited to, adhesives, thermal bonding, pressure bonding, mechanical entanglement, hydroentanglement, ultrasonic bonds, microwave bonds, or any other conventional technique. The bonding of edge 146 to the cover ribbon 136 can form a bonded edge 56. The discrete combination 134 of the contact member 52 and the outer sheath 110 can have a second edge, such as edge 148, which remains unbound from the cover ribbon 136 and can form, therefore, a free edge 58. The cover ribbon 136 can undergo a separation process, such as, but not limited to, knife cutting, wherein an individual unit having a cover 34, a contact member 52 and an outer sheath 110 is separated from the cover ribbon 136. In such an embodiment, the individual unit of the cover 34, the contact member 52 and the outer sheath 110 can be bonded to a nonwoven ribbon 32, a fleece 30, a blank 28 or a pledget 12 as described above.

It is to be understood that, in some embodiments, when the cover 34 and contact member 52 combination are bonded to the nonwoven ribbon 32, the fleece 30, the blank 28, or the pledget 12, a portion of the free edge 58 of the contact member 52 may become bonded to the overall structure dependent upon how and where the cover 34 and contact member 52 combination is bonded to the structure such as the nonwoven ribbon 32, the fleece 30, the blank 28, or the pledget 12. In such embodiments, at least about 70, 75, 80, 85, 90, or 95% of the free edge 58 remains free from bonding.

Figure 20:
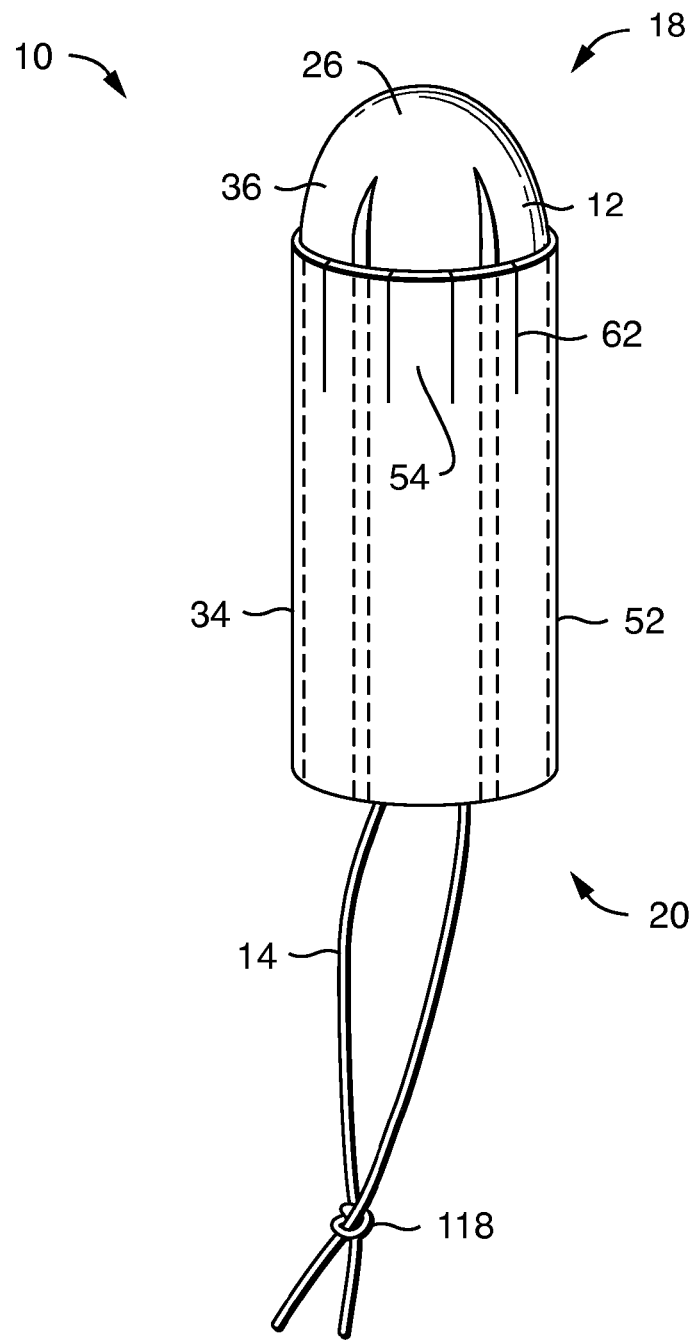
FIG. 20 is a perspective view of an embodiment of a tampon in which the cover is a contact member.

In an embodiment, the cover 34 and the contact member 52 can be integral with each other. FIG. 20 illustrates such an embodiment in which the cover 34 can be the contact member 52. In an embodiment, the cover 34 can extend beyond the insertion end 18, the withdrawal end 20, or combinations thereof. In such an embodiment, the cover 34 can be provided with at least one slit 62 as described herein. In an embodiment, the cover 34 can be provided with at least one, two, three, four, five, six, seven, eight, nine, or ten slits 62. The cover 34 can have at least one contact element 54 as described herein. The cover 34 can have as many contact elements 54 as deemed suitable.

As noted above, the nonwoven ribbon 32 can be separated into individual units of fleece 30 which can be rolled, stacked, folded or otherwise manipulated into blanks 28 before compressing the blanks 28 into pledgets 12. For example, suitable menstrual tampons may include "cup" shaped pledgets like those disclosed in U.S. Publication No. 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310,269 to Friese; "sausage" type or "wad" pledgets like those disclosed in U.S. Pat. No. 2,464, 310 to Harwood; "M-folded" tampon pledgets like those disclosed in U.S. Pat. No. 6,039,716 to Jessup; "stacked" tampon pledgets like those disclosed in U.S. 2008/0132868 to Jorgensen; or "bag" type tampon pledgets like those disclosed in U.S. Pat. No. 3,815,601 to Schaefer.

A suitable method for making "radial wound" pledgets is disclosed in U.S. Pat. No. 4,816,100 to Friese. The radial winding method can also include a method for compressing the blank into a pledget like that disclosed in U.S. Pat. No. 6,310,269 to Friese. Suitable methods for making "W-folded" pledgets are disclosed in U.S. Pat. No. 6,740,070 to Agyapong; U.S. Pat. No. 7,677,189 to Kondo; and U.S. 2010/0114054 to Mueller. A suitable method for making "cup" pledgets and "stacked" pledgets is disclosed in U.S. 2008/0132868 to Jorgensen.

In various embodiments, the blank 28 can be compressed into a pledget 12. The compressing step can utilize any suitable means and apparatus. For example, the compressing step may utilize a plurality of dies which reciprocate relative to one another so as to form a mold cavity therebetween. When the blank 28 (e.g., a softwind) is positioned within the mold cavity, the dies may be actuated so as to move towards one another and compress the blank 28. The blank 28 may be compressed any suitable amount. For example, the blank 28 may be compressed at least about 25%, 50%, or 100% of the initial dimensions. For example, a blank 28 can be reduced in diameter to approximately ¼ of the original diameter. The cross-sectional configuration of the resultant pledget 12 may be circular, ovular, rectangular, hexagonal, or any other suitable shape.

In various embodiments, the compressing step may not include any additional heat applied to the pledget 12. In other words, the blank 28 can be compressed into a pledget 12 without external heat being applied to the compression equipment or the blank 28. In various embodiments, the compressing step may incorporate or may be followed by one or more additional stabilization steps. This secondary stabilization can serve to maintain the compressed shape of the pledget 12. In general, the secondary stabilization step can create hydrogen bonds between the absorbent fibers and/or may further strengthen the entanglement of the absorbent fibers to maintain the shape of the compressed pledget 12.

In various embodiments, the pledgets 12 may be subject to further processing to result in a finished tampon. For example, the pledgets 12 may be joined with a withdrawal aid 14 and/or applicator.

The withdrawal aid 14 may be attached to the pledget 12 in any suitable manner. For example, an opening can be formed through the pledget 12 (and cover 34 if provided) so as to provide a means for attaching a withdrawal aid 14. In various embodiments, the withdrawal aid 14 can be attached to the fibrous material 138 before or after it is compressed into the pledget 12. The withdrawal aid 14 can be attached to the fibrous material 138 and then looped upon itself. A knot 118 can then be formed near the free ends of the withdrawal aid 14 to assure that the withdrawal aid 14 does not separate from the fibrous material 138. The knot 118 can also serve to prevent fraying of the withdrawal aid 14 and to provide a place or point where a woman can grasp the withdrawal aid 14 when she is ready to remove the tampon 10 from her vagina.

The withdrawal aid 14 can be constructed from various types of threads or ribbons. A thread or ribbon can be made from 100% cotton fibers and/or other materials in whole or part. The withdrawal aid 14 can be bonded to the absorbent fibers with or without tying. The withdrawal aid 14 can have any suitable length and/or the withdrawal aid 14 can be dyed and/or treated with an anti-wicking agent, such as wax, before being secured to the pledget 12.

In various embodiments, the tampon 10 may also include one or more additional features. For example, the tampon 10 may include a "protection" feature as exemplified by U.S. Pat. No. 6,840,927 to Hasse, U.S. 2004/0019317 to Takagi, U.S. Pat. No. 2,123,750 to Schulz, and the like. In some embodiments, the tampon 10 may include an "anatomical" shape as exemplified by U.S. Pat. No. 5,370,633 to Villalta, an "expansion" feature as exemplified by U.S. Pat. No. 7,387,622 to Pauley, an "acquisition" feature as exemplified by U.S. 2005/0256484 to Chase, an "insertion" feature as exemplified by U.S. Pat. No. 2,112,021 to Harris, a "placement" feature as exemplified by U.S. Pat. No. 3,037,506 to Penska, or a "removal" feature as exemplified by U.S. Pat. No. 6,142,984 to Brown.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a tampon, the method comprising the steps of:
   a. providing a fibrous material;
   b. providing a cover;
   c. providing a contact member comprising a first edge and a second edge;
   d. incorporating at least two slits in the contact member to form a contact element in the contact member;
   e. bonding one of the first edge or the second edge of the contact member to the cover to create a bonded edge and a free edge;
   f. bonding the combination of the cover and the contact member to the fibrous material; and
   g. compressing the combination of the fibrous material, the cover and the contact member.

2. The method of claim 1 further comprising the step of separating at least one individual unit from the fibrous material.

3. The method of claim 1 further comprising the step of rolling, stacking or folding the fibrous material.

4. The method of claim 1 wherein the fibrous material is one of a nonwoven ribbon, a fleece, and a blank.

5. The method of claim 1 further comprising the step of enclosing the contact member in an outer sheath.

6. The method of claim 5 further comprising the step of incorporating at least two slits in the outer sheath.

7. A method of manufacturing a cover for a tampon, the method comprising the steps of:
   a. providing a cover ribbon;
   b. providing a contact member comprising a first edge and a second edge;
   c. incorporating at least two slits into the contact member to form a contact element;
   d. bonding one of the first edge or the second edge of the contact member to the cover ribbon to create a combined unit of cover ribbon and contact member with a bonded edge and a free edge; and
   e. separating the combined unit of cover ribbon and contact member from a remainder of the cover ribbon.

8. The method of claim 7 further comprising the step of enclosing the contact member in an outer sheath.

* * * * *